United States Patent
Valles et al.

(10) Patent No.: US 8,034,333 B2
(45) Date of Patent: *Oct. 11, 2011

(54) SOLENOPSIS INVICTA VIRUS

(75) Inventors: Steven Valles, Gainesville, FL (US); Roberto M Pereira, Gainesville, FL (US); Wayne B Hunter, Port St. Lucie, FL (US); David H Oi, Gainesville, FL (US); Charles A Strong, Gainesville, FL (US); Phat M Dang, Port St. Lucie, FL (US); David F Williams, Gainesville, FL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/780,854

(22) Filed: Jul. 20, 2007

(65) Prior Publication Data

US 2008/0031856 A1    Feb. 7, 2008

Related U.S. Application Data

(62) Division of application No. 11/239,183, filed on Sep. 29, 2005, now Pat. No. 7,332,176.

(51) Int. Cl.
*A01N 63/00* (2006.01)
*A01N 25/00* (2006.01)
*A01N 25/08* (2006.01)

(52) U.S. Cl. .......... 424/93.6; 424/405; 424/410

(58) Field of Classification Search ............... None
See application file for complete search history.

(56) References Cited

OTHER PUBLICATIONS

Valles et al., 2004, Virology, 328: 151-157.*
Williams et al., 2003, American Entomologist, 49: 150-163.*
Avery et al., 1977, The Florida Entomologist, 60: 17-20.*
Cameron et al., 2000, PNAS, USA, 97: 9514-9518.*

* cited by examiner

*Primary Examiner* — Joanne Hama
(74) *Attorney, Agent, or Firm* — John D. Fado; Gail E. Poulos

(57) ABSTRACT

Unique *Solenopsis invicta* viruses (SINV) have been identified and their genome sequenced. Oligonucleotide primers have been developed using the isolated nucleic acid sequences of the SINV. The viruses are used as a biocontrol agent for control of fire ants.

4 Claims, 18 Drawing Sheets

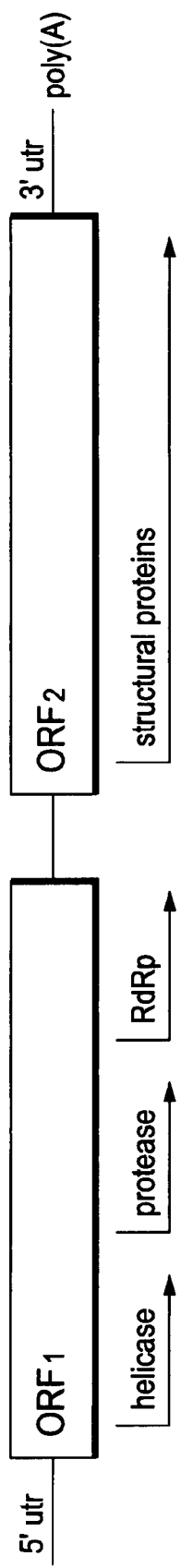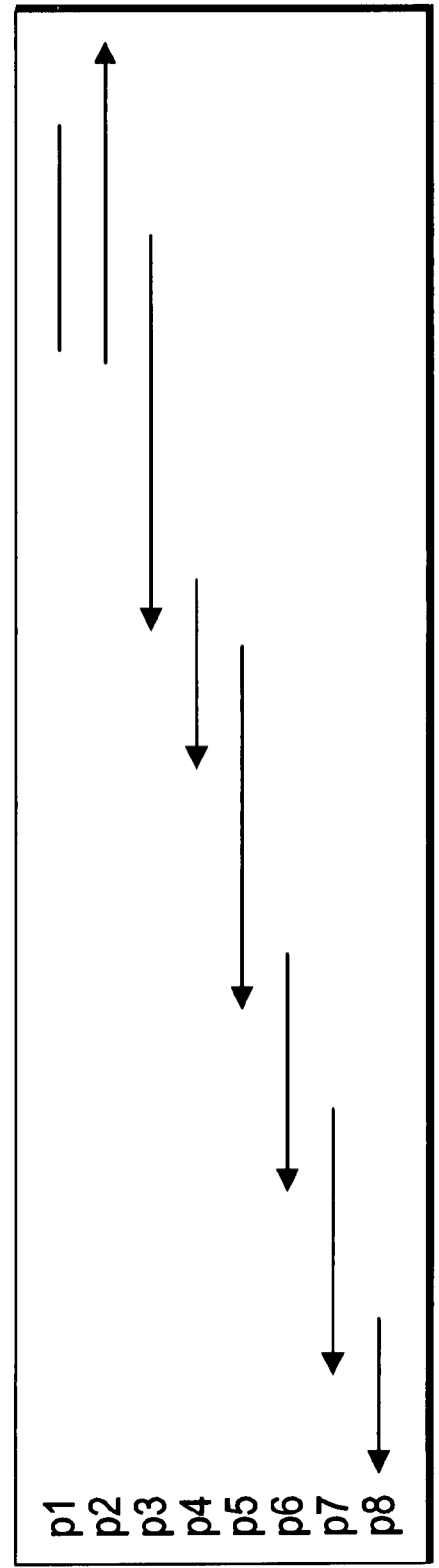
Fig.1a
Fig.1b

```
   1 catcgagatc tattgctacc cttccaaatg catatgaagt tgttggctga cttggttaag
  61 atggttgata cctcaggcgc atttgggacc aaacctcgaa cccaaccagt tgtgatttgg
 121 ttgtttggtg aaagtggcgt aggtaagtca ggcatgtcct ggccctagc cattgatctg
 181 aataatattt tcatgacaaa taaggaagat gcccgaact tctcgcgcaa catatatatg
 241 cgaaatgttg agcaggagtt ttgggacaat tatcaaggac aaaacgtagt tatatatgat
 301 gattttggac aacgcaaaga tcccaagca aaacccaacg aagaattcat ggaattgatt
 361 cgtacagcta acatcgctcc atatccttta catggcac atttagaaga taaacgaaag
 421 actaaattta catcaaaat tctacttatg acatccaacg ttttttgaaca gagtgtagat
 481 tctttaacct ttcctgatgc tttccgtagg cgcattgacc tgtgtggtcg cgtgtccaat
 541 aaaccacaat ttaccaaacc aggttttttca aaagcaactg gtcaaactgt taaaagattg
 601 gacaaagata gggttagaaa agaattcaat caagttattt caacagacgt ttatttaata
 661 gatttaattg acgcagagac tggtgatgtc attgaagaag gattggatta tgcagaattc
 721 ctagaacgag caacacagaa aactaacgaa gcattcaatc aatccgtaga attaaatgaa
 781 ttttagaga attatgcaga tcccgatat cgactagcaa caatgcaggt aggcgatgaa
 841 tttcatgact gtaataattt attacttatt aagatagaaa actttgatga tttacctagc
 901 aatacgcttt tatttgattc acaaggaaat tccaaatcta acgagaaat tgaggaaaat
 961 ttacagaatg catgggtggc aatggaagaa gacacttcga tgtggcacga ttcttattat
1021 aattttagag atgacatagt gtataaaag tataaagat cagtatcaga tagagagttt
1081 acactaatga aggcatatga gtattttaag aaacaatctt ctaaattttt gaacgataca
1141 ctaacgtata tcaaagaaca cccatttaaa gctgtagctg gagtaatgat agcagttttt
1201 accttgatga ccataggcaa ttttggtct tctttctggt cgaaaccaga gagagatagg
1261 acaacaaaga tgacgggtcg tcagcarggt aatattgttg aattgcccta cagaggkgaa
1321 gaagcgatag atttaagaca tcttgaggaa aaacaattaa tagaytattt gcaccatttt
1381 acatcttcag cgttrgcagg ctcaacatat gcgttcatat ttaaccaacc caatgctgtt
1441 gcctacggta tcttaacagg tgccgtagaa acggcgattg tttatatata cgacaaattt
1501 aggcaacatg gtaaaactgt gacgccagag gttgaagcag caacttcagg tgattgtatg
1561 acgaaagtga acctcgcgt cattctggag gccacaacat ccggtgatgc acaaacgcag
1621 tatagatcta aaccaaaat tgaagcattc acgtcggcgg atgtaataac cattactaaa
1681 cccaaagtga tggttgaggc agtgtcatct ggcgatagta taactcaaaa caaacctaaa
```

Fig. 10a

```
1741 gctaagattg aggcaatgac atctggtgac tcacatacca tggtgaaacc taaggctaaa
1801 atagaagcac aaacttcagg agataatatt acaatagtga gacctaaaat actaacagaa
1861 ggagatatta taccagcgaa tatgcaaatg tggaaggatc aagttgcaca aaatttaatt
1921 acccatcgta ttttcaacaa tttatataaa atttcggcta ataattgttc agttcccttg
1981 atgcatggtc ttatggttaa aggacgtatt atgcttattc cagcccacat tttaggatgt
2041 ggtataaaag cagatactga aattaccatg gagaatatgt ttaaagttaa atttacattc
2101 cctttcaaga gcgttaaagt aacccgcata actaatcgac atggagagtc aaaggaagct
2161 tgtttatttg ggcttccaaa tttggttcat acgcattgtg atattactaa acatttttca
2221 gattcagaag caatgtcatc ttattcacgt gcggaagtta acttaccttt attgcgatat
2281 tcccaacatt tagatagctt tatagtacac attctttcag ctaatgatgc atttgcaatt
2341 gaccatccca taattcttaa tgatgtagac ttgggcaaac atgttgtgag aagagcattg
2401 gaatatacag caccaacaac aaacggcgat tgtggcgcac cattaatcat caatgaaccc
2461 tctgtcttgc gaaagatagc aggaattcat gttgcaggtg acgccatgg acgagcttat
2521 tcagaatcaa ttacacaagc tgatttaact cgagcttatc ctgaatttcc agcgcgaatg
2581 caaatttgtc tggactggga taataaaatg aagtttcacc caattgagat taagcaagaa
2641 tacaccaaag ctgactttcc atatgctcca ggagacatgt tggtcccat aggtaagtgc
2701 ccccaccagt tatttgagcc cggtaaaaca gatattcgac ctagtgtaat ttatggtaag
2761 gtaaaacctc ctattacgaa acccgctatt ttacggcatt ccgaagttaa tatgaaattt
2821 aagaatttgc aaaaatgtgc ttcaaacgta ccgtacatta tgaagattg gcttgaggaa
2881 gcatatttag atgtaaagca attatggaat tctaaaagaa atgatgcgtt tcggcggatt
2941 ttaacagatg aagaagtaat taaggaaat gatatttcag aatatatttc tagtataaat
3001 cgacaatcat ccccaggtta cccatggatt ttagatcgta accaggctt tccaggtaag
3061 actcaatggt ttgggaacga tgaagattac aaaattgatc ctgacgtgat gcaaaaagta
3121 catgaaagaa ttgaaaacgc aaaacaagga atacggaccc caacttttg ggttgacacg
```

Fig. 10b

```
3181 ctcaaggatg agcgacgacc tattgagaaa gttgatgcac tcaaaacacg cgtctttcg
3241 aacggaccca tggatttaa tttggctttc cgcaaatatt ttctaggatt tatagcgcat
3301 ttaatggaaa atcgaataga taatgaagta gcaataggca ccaacgtata tagtagagat
3361 tggacaaaac tggctaagaa attaaaacag aaaggtaaga acgttttgc aggggatttt
3421 tcaaattttg atggatcctt aaatgccatg attatgtatt tgtttgcccg gatggcaaac
3481 gaattctatg atgatggtaa tgacctgatc cgttatgttt taattgagga gattttgaat
3541 tcagtacatc tttgtgaaca attcttctat atgatgaccc attcccaacc atctggcaat
3601 cctgcaacca ctcccttaaa ttgcttgatc aattcgatag gttgcggtt gtgtttcctc
3661 cggtgttttg aagaacacaa ggccttcttt atggaactta tgaagaaatt tggctgtaaa
3721 acacggatgg agctattcag attgctagta tcactgatat cctatggaga tgataatgta
3781 atcaatattc acccctgat ttcccattta ttcaatatga atacaatcac aaaatacttt
3841 gcggaatttg gatttacata tacagatgaa acaaagcaag taggaaaagg agtgcctgat
3901 tataaaactc tggaagaagt ttcgtttctc aagagaggat ttatcttcaa tgaggagcga
3961 aattgttatg atgcgccctt ggacatcaat acaattctag atgattaa ttgggtccgg
4021 aaagatttgg atcaagtgga gagcactaag attaattgtg aaaatgcaat tatggaattg
4081 gctatgcatc cacgggctgt ttttgataag tggacccac agatcgagaa agcttttat
4141 gacaaaactg gcgtggtctt gaaccacaat tcwtatgacg gctattggca tttacgaaat
4201 atggaatact ttttataaaa cgttctctt ctggttacca gcaacatagg aaattgtcgt
4261 tgaactacat gttgtaaggc tttagagaaa taagggagtg tcctatttag gatgaggtgc
4321 tccggtggca gccccaccaa aacctctagc gactaggaac agctatatcg ggttgctata
4381 gcagtcagga tgtcattctg cgttcgaa atacccaaac ctgctcaatc aaacaatgcg
4441 aatacttttg agacgaaaac ggcaacaacc tctgcttccc acgcacaatc ggaacttagc
4501 gagacgaccc cagaaaattc ccttaccaga caagaactca cagttttcca tgatgttgaa
4561 caacctcgcg tcgctcttcc aattgctccg caaacgacta gctctcttgc taagcttgat
4621 tctacagcga caattgtgga ttttctttct agaactgttg tcctcgatca attcgagctt
```

Fig. 10c

```
4681 gttcaaggtg aatcaaacga taaccacaaa cccottaacg cagcaactto taaagacccc
4741 caaccagcca tcagacagta ttccttgcca ggagacatto ttaagctggg tggcaagtta
4801 gataaggcaa ataaccatca atactttaag gcagattgtc acataaaatt agtttaaat
4861 acaaatccca tggtggccgg aagattttgg ctaacatatt ccccatatga acataaagta
4921 gataaggcaa gacgccagca atataatagt agagctggag tgacagcata tcctggaata
4981 gaaatggatg ttcaaatcaa tgattcagca gaaatggtta tcccatttgc ttcctacaaa
5041 gaagcttatg atttaaatac tcccaccoct gaagattttg ttacattatc tttattcggt
5101 ataacagatt tactagctaa aaatggtaat aattacgcag taggaattac catcttagcc
5161 tggtttgaaa acataacaat taatctacct acaataaaga atatcccata caggcaatta
5221 ccccacacca atactaatac taagaaaatt gaaatagatc gcaaattagc taaattagaa
5281 aagaagaatc cttcggccta taaatatata actaatattt tagatatacg accagccacc
5341 atgcaaaccg catggggtgc cccatcacag ttgctaatta aagatattct agatctagca
5401 ccagtgctta atgaacttca agcagtattg tctgatgtgt gtggatcaat taggaaccga
5461 gacttttcgt tgaggccctt gtataaagta cgcatacatg caatgcaaga cttaatcaat
5521 gattccctaa agaggatgtt tgatacatat gaggccctgg acgagacgga tcttatgagt
5581 gaagacacac cagataatgc ttttccaact atggttttat acttagattc ccttaagaaa
5641 attaacaagt caaaatcaga gtatgttgag atgcagttgg atgcctatga tgcacgggat
5701 attgatggta tgctgaatgc gtacgatcaa ttgaaagagt ttaaccatca tacagcaaga 5761 aaggaaatgg tgtcaatgat gcatctgggc taccaatatt ctcaacgacg acaccgacgt
5821 gatgtgacag cagcgagagc catagcggat atgatacttg tcgacgagcg tgatgcgacg
5881 atgcaagtgc aagcagaagt aggaggacag ggtttgatca ctgacatagc ttccaccgtt
5941 tcggcggtgg caggtgcggt cagtggtatc cctgtcatac gtgaaatagc atctaccgtt
6001 ggttgggttt ctgacatagt tggaggaatt tcctctatct ttggatggtc tcgaccaaat
6061 gatatggaga aagtgacatc tttggctaac gtccccggca agtattattc ccatgtaaaa
6121 gcgatagata atagtgtagc tttagctttg agtaatgaga acgagcttct cccacttagc
```

Fig. 10d

```
6181 gacatctttc cctcagcggt agatgagatg gacttggcat atgtgtgtgc taatcctgga
6241 gtgaaggaag tcattacgcg gtcgaaaacg gacccyatga atagaacttt agctttaatg
6301 gaagtgggat tacctagttt taatagatac caagataagg caatagattg tgatagtgaa
6361 cctaccccat ataatatctg taacaaagrt ttgatcaaac caaatgggaa catcattttg
6421 agccctggag atctggtgca gatgaaggc agcttggctg cgacaatttt ggatactgtt
6481 ccttgtgaat atgtgtccca attgtttcag tattggcgtg ctaccatttg ctttaagatt
6541 tctgtggtaa agaccggttt tcatacagga cgtttagaaa ttttctttga cccgggtgag
6601 tatctaacga atcctaaggc ggattggcat aattatgttg atctttccgc ttacgataaa
6661 gtggataccg caaattctta caaatatatt ttagatttaa caaatgattc agaaattact
6721 attagagtgc catttattag cgataggtta gctttaagta caattggtgc taatagttat
6781 ggtgaggacg gtgtaatggg acccccaaat ttgaatgata ttttcgattc aatgattggg
6841 tctctaatca tcagaccgct tacaaaactt atggcgccag atacagtttc agatcaagtt
6901 aaaatagtaa tttggaaatg ggcagaggat gtacagctcc ttgttcccaa agaatcgaac
6961 cagctcgaaa tagttccata cgagttcgag cgaacaccag gtttgacctg caagaaacag
7021 aaaatatcag atgaagatat gaaggtgttt attgcacatt gggaaaaaga tggcaaatgg
7081 atttgtactt cagacccaac tacaagcatg gttttctcat ggggacaata tcccttatgt
7141 gagactagaa atgccacaat gcagatcaac atttccaatg aagcatcagg aaacagtatc
7201 gatatttttcc aggataataa tgcaggtgtg agtccaaatg cagtaatggg taaaattgcg
7261 ggtgaacgtc tagttaactt gcgaccacta ctgcgctgct tccgatcttt gggtggcata
7321 acgcttgatc gggcaggaca aattctgtct gaaagagtgt attggaacca caaagattat
7381 gttagcatac tctcatatct gtatcgtttt tccagagggg gatatcgtta caaattcttt
7441 gcagacgata acgaacaggg acaagtcatg tcaacgcttg tcaaaaatta ctacaaggac
7501 catgcaacaa gtactggtcc atcccatatg acttacaata atattaatcc cgtacatgaa
7561 attatgatcc catattattc tcaatatagg aaaatcccaa tttcaggcga agtagaatta
7621 attaaaggta agattcaaac tcccgtagaa aagggcatta aggtgagct ttatcgctca
7681 ggaaatgatg acctaaccta tgggtggatc gttggatcgc cccagcttta tgttggagcg
7741 gctcaacgat ggagttgttg gacagtaaca aagccaacac aactagtcac taaggaaact
7801 taatggatag taaattttgc tcttcaaaga cagtcaaatc tttggagttc ggttttattc
7861 ttcaaaattc ttttaaaaca gaggatgcat agttaatggc gagcactatc gtccggaatg
7921 acaccgttga gaaaactcac tagatggagg ctcattggtt atcagcgttc tgggataatc
7981 taacgattag ttatgcaaac gcatattcaa gtaaattaca attaag
```

Fig. 10e

```
   1 taatctacct acaataaaga atatcccata tagacaatta ccccaaacta ataccaatgc
  61 aaagaagatt gaaatagatc gaaaattggc taaattagaa aagaagaacc cttccgctta
 121 taaatatata actaatattt tagatatacg gccggccacc atgcagaccg catggggcac
 181 tccatcacaa ttattaatta aggatgtttt agatttagca ccggtattta acgaacttca
 241 agcagtatta tctgaagtgt gtggatcaat taggaaccga gacttttcgt tgaggccttt
 301 atataaagta cgcatacatg ctatgcaaga cttaatcaat gattccttaa agaggatgtt
 361 tgatagatat gaggccctgg acgagacgga tcttatgagt gaagacacac cagataatgc
 421 tttcccaact atggttttat atttggattc ccttaagaaa attaataagt caaaatcaga
 481 gtatgtggag atgcaattgg atgcctatga tgcacgagat attgatggta tgttaaatgc
 541 atataatcaa ttgaaagagt ttaatcacca tacagcaaga aaggagatgg tgtcaatgat
 601 gcatctgggt tatcaatatt cccaacggcg gcaccgacga gatgtaacag cagcaagagc
 661 catagcagat acaatacttg tagatgaacg cgatgcaaca atgcaagtcc aagcagaagt
 721 aggaggacag ggtcttatta ctgacatagc ctctaccgtt tcggcggtgg cggtgcagt
 781 cagtggtatc ccggttatag agaaattgc atctacagtt ggtgggttt ctgatatagt
 841 tggaggaatt tcctccatct ttggatggtc tcgaccaaat gacatggaaa aagtaacatc
 901 tttggcaaac gttcctggca agtattattc tcacgtaaaa gcagtagata atagtgtagc
 961 tttagctttg agtaatgaga acgaacttct cccgcttagt gacatctttc cctcagcagt
1021 agatgagatg gatttggcat acgtgtgtgc caaccccgga gtgaaggagg tcattacatg
1081 gtcgaagaca gatcccatga ataagacttt agcattaatg gaagtaggat tacctagttt
1141 taatagatat caggataagg caatagattg tgatagtgaa cccactccat acaacatttg
1201 taataaagat ttaattaaac caaatgggaa tattatttg agccctgggg atctggtgca
1261 gatgaaggt agcctggctg cgacaatctt ggacactgtt ccatgcgaat acgtgtctca
1321 gttgtttcag tattggcgtg ctacaatttg ctttaagatt tccgtggtga aaactggttt
1381 ccatacagga cgtttggaga ttttctttga ccctggtgag tatcttacta atcctaaggc
1441 ggattggcat aattatgttg atctttcggc ttatgataag gtggatactg caaattctta
1501 caaatatatt ttagatttaa cgaatgattc agaaattacc attagagtac catttattag
1561 tgataggtta gctttaagca caatcggtgc caatagttat ggtgaggatg gtgtgatggg
1621 accccaaat ttgaacgata ttttcgattc aatgattggg tctctgatca tcaggccgct
1681 cacgaggctt atggcgccag atacagtttc agatcaggtt aaaatagtaa tttggaaatg
1741 ggctgaagat gtgcagctcc ttgttcctaa agaatcaaat caactcgaaa tcgttccata
1801 cgagtttgag cgaacaccag gtttgacatg caagaaacaa aagatttctg atcaagatat
1861 gaaggtgttt attgcgcatt gggaaaaaga tggtcaatgg gtttgtactt cagacccaac
1921 cacaagcatg gtcttttcat ggggacaata tcccttatgt gagaccagaa atgctacgat
1981 gcagataaac atttctaatg aagcttcagg aaatagtatt gatattttcc aggataataa
2041 tgcaggtgta agtccaaacg cagttatggg gaaaattgca ggtgaacgtt tagttaacct
2101 acgaccatta ttgcgatgct ttcgttcctt gggtggcata acgctggatc gggcaggtca
2161 aatcctgtct gagagagtgt attggcatta taaggattac gttagcatac tttcatacct
2221 gtatcgattt tctagaggag gatatcgcta caagttttt gcagatgaca acgaacaagg
2281 acaagtcatg tcaacgcttg ttaaaaatta ccacaaggac catgctacaa gcactggtcc
2341 ttcccatatg acttacaata atctccaacc cgtacaggaa attatgatcc catattattc
2401 tcaatatagg aaaattccaa tttcaggcga gtagaattaa attaaaggta agattcagac
2461 acctgtagaa aagggcatta aagtgagct ttatcgctca ggaaatgatg acctgacata
2521 cgggtggatc gttggatcgc cccaacttta tgttggagca gctcaacggt ggagttgttg
2581 gacagtaaca agccaacac aactaggcac taaggaaact taatggatag taaatttgc
2641 tcttcaggga cagtcaaatc tctggagttc ggttttattc ttcaaaattc ttttaaaaca
2701 gaggacgtat gtggaatggc gagcactatt gttcggattg acgattttga gaaaactcac
2761 tagatggagg ctcttgatct attagcagtc tgagataatc taacgatttc acatgcgaac
2821 gcatattcaa gtaaattaaa ttaagaaaaa aaaaaaaaa aaaa
```

Fig. 11 tgtctgaaag agtgtattgg aaccacaaag attatgttag catactctca tatctgtatc
gtttttccag aggggatat cgttacaaat tcttcgcaga cgataacgga cagggacaag
tcatgtcaac gcttgtcaaa aattactaca aggaccatgc aacaagtact ggtccatccc
atatgactta caataatatt aatcccgtac atgaaattat gatcccatat tactctcaat
ataggaaaat cccaatttca ggcgaagtag aattgattaa aggtaagatt caaactcccg
tagaaaggg cattaaaggt gagctttatc gctcaggaaa tgatgaccta acctatgggt
ggatcgttgg atcgcccag ctttatgttg gagcggctca acgatggagt tgttggacag
taacaaagcc aacacaacta gtcactaagg aaacttaatg gatagtaaat tttgctcttc
aaagacagtc aaatctttgg agttcggttt tattcttcaa aattcttta aaacagagga
tgcatagtta atggcgagca ctatcgtccg gaatgacacc tttgagaaaa ctcactagat
gga

Fig. 12 tgtctgaaag agtgtattgg aaccacaaag attatgttag catactctca tatctgtatc
gtttttccag aggggatat cgttacaaat tcttcgcaga tgataacgaa cagggacaag
tcatgtcaac gcttgtcaaa aattactaca aggaccatgc aacaagtact ggtccatccc
atatgactta caataatatt aatcccgtac atgaaattat gatcccatat tattctcaat
ataggaaaat cccaatttca ggcgaagtag aattaattaa aggtaagatt caaactcccg
tagaaaggg cattaaaggt gagctttatc gctcaggaaa tgatgaccta acctatgggt
ggatcgttgg atcgcccag ctttatgttg gagcggctca acgatggagt tgttggacag
taacaaagcc aacacaacta gtcactaagg aaacttaatg gatagtaaat tttgctcttc
aaagacagtc aaatctttgg agttcggttt tattcttcaa aattcttta aaacagagga
tgcatagtta atggcgagca ctatcgtccg gaatgacacc tttgagaaaa ctcactagac
gga

Fig. 13 tgtctgaaag agtgtattgg aatcacaaag attatgttag catactctca tatctgtatc
gtttttccag aggggatat cgttacaaat tcttcgcaga cgataacgaa cagggacaag
tcatgtcaac gcttgtcaaa aattactaca aggaccatgc aacaagtact ggtccatccc
atatgactta caataatatt aatcccgtac atgagattat gatcccatat tattctcaat
ataggaaaat cccaatttca ggcgaagtag aattaattaa aggtaagatt caaactcccg
tagaaaggg cattaaaggt gagctttatc gctcaggaaa tgatgaccta acctatgggt
ggatcgttgg atcgccccag ctttatgttg gagcggctca acgatggagt tgttggacag
taacaaagcc aacacaacta gtcactaagg aaacttaatg gatagtaaat tttgctcttc
gaagacagtc aaatctttgg agttcggttt tattcttcaa aattctttta aaacagagga
tgcatagtta atggcgagca ctatcgtccg gaatgacacc tttgagaaaa ctcactagat
gga

Fig. 14 tgtctgaaag agtgtattgg aaccacaaag attatgttag catactctca tatctgtatc
gtttttccag aggggatat cgttacaaat tcttcgcaga cgataacgaa cagggacaag
tcatgtcaac gcttgtcaaa aattactaca aggaccatgc aacaagtact ggtccatccc
atatgactta caataatatt aatcccgtac atgaaattat gatcccatat tattctcaat
ataggaaaat cccaatttca ggcgaagtag aattaattaa aggtaagatt caaactcccg
tagaaaggg cattaaaggt gagctttatc gctcaggaaa tgatgaccta acctatgggt
ggatcgttgg atcgccccag ctttatgttg gagcggctca acgatggagt tgttggacag
taacaaagcc aacacaacta gtcactaagg aaacttaatg gatagtaaat tttgctcttc
aaagacagtc aaatctttgg agttcggttt tattcttcaa aattctttta aaacagagga
tgcatagtta atggcgagca ctatcgtctg gaatgacacc attgagaaaa ctcactagat
gga

Fig. 15 tgtctgaaag agtgtattgg aatcacaaag attatgttag catactctca tatctgtatc
gtttttccag aggggatat cgttacaaat tcttcgcaga cgataacgaa cagggacaag
tcatgtcaac gcttgtcaaa aattactaca aggaccatgc aacaagtact ggtccatccc
atatgactta caataatatt aatcccgtac atgagattat gatccatat tattcccaat
ataggaaaat cccaatttca ggcgaagtag aattaattaa aggtaagatt caaactcccg
tagaaaaggg cattaaaggt gagctttatc gctcaggaaa tgatgaccta acctatgggt
ggatcgttgg atcgcccag ctttatgttg gagcggctca acgatggagt tgttggacag
taacaaagcc aacacaacta gtcactaagg aaacttaatg gatagtaaat tttgctcttc
aaagacagtc aaatctttgg agttcggttt tattcttcaa aattctttta aaacagagga
tgcatagtta atggcgagca ctatcgtccg gaatgacacc tttgagaaaa ctcactagat
gga

Fig. 16 cactccatac aacatttgta ataaagattt aattaaacca aatgggaata ttgttttgag
ccctggggat ctggtgcaga tgaaaggtag cctggctgcg acaattttag acactgttcc
atgtgaatac gtgtctcagt tgtttcagta ttgg

Fig. 17 cactccatac aacatttgta ataaagattt aattaaacca aatgggaata tcattttgag
ccctggggat ctggtgcaga tgaagggtag cctggctgcg acaattttgg acactgttcc
atgtgaatac gtgtctcagt tgtttcagta aagg

Fig. 18

SOLENOPSIS INVICTA VIRUS

This is a divisional of application Ser. No. 11/239,183 filed Sep. 29, 2005 now U.S. Pat. No. 7,332,176, which is herein incorporated by reference in its entirety.

BACKGROUND OF THE INVENTION

1. Field of the Invention

This invention relates to biological methods and products useful for the control of *Solenopsis invicta*. More specifically, the present invention is directed to novel *Solenopsis invicta* viruses, nucleic acids encoding the novel viruses, biocontrol composition, and methods of using the viruses and/or biocontrol compositions for control of fire ants.

2. Description of the Related Art

Red imported fire ant, *Solenopsis invicta* (Buren), was first detected in the United States near Mobile, Ala. in the late 1920s (Loding USDA Insect Pest Surv. Bull., Volume 9, 241, 1929). Since that time, it has spread to encompass more than 128 million hectares, primarily in the southeastern United States (Williams et al., Am. Entomol., Volume 47, 146-159, 2001). Fire ants are known to destroy young citrus trees, growing crops, and germinating seeds. This has an economic impact on agriculture in infested areas. Telephone companies spend substantial amounts of money each year treating their electrical equipment to prevent fire ant invasion because fire ants accumulate at electrical contacts and can short out electrical equipment. Even, farm equipment can be damaged by large fire any mounds. Fire ants also present a danger to parameters that can be modified to wildlife, such as ground nesting birds and animals. Furthermore, fire ants are known to excavate the soil from under roadways causing damage.

Fire ants also pose health care problems to millions of people stung each year-a significant number of which require medical care. Fire ant stings are also blamed for human deaths. Consequently, there is much interest in controlling these troublesome pests.

This interest has resulted in much research and resources being expended through the years to develop reagents and methods for controlling fire ants. While many useful insecticide formulations have resulted from this research, the problems associated with fire ants still exist because the relief gained by insecticide use is only temporary. Once the insecticide pressure is relaxed, fire ant populations invariably repopulate the areas. This reinfestation ability is attributed to the high reproductive capabilities, the efficient foraging behavior, and the ecological adaptability of the ants. While effective for controlling ants in relatively small defined areas, insecticides can create other problems. For example, some insecticides, which are effective at controlling fire ants, can pose a significant threat to the environment, including birds and animals.

Although considerable research effort has been brought to bear against the red imported fire ant, it remains the primary pest ant species in infested areas; initial eradication trails fails, yielding to the wide distribution of pesticide-based control products and a federally imposed quarantine to prevent further spread. Recently, much of the research effort has focused on elucidating basic life processes in an attempt to develop unique control measures, and fostering the development of self-sustaining methods of control, including biocontrol organisms and microbes (Williams et al., Am. Entomol., Volume 49, 150-163, 2003).

A dearth of natural enemies of the red imported fire ant have been found including a neogregarine (Pereira et al., J. Invertebr. Pathology, Volume 81, 45-48, 2002) and a fungus (Pereira et al., J. Invertebr. Pathology, Volume 84, 38-44, 2004).

U.S. Pat. No. 6,660,290 discloses a non-sporulating mycelial stage of an insect-specific parasitic fungi for control of pests with fire ants listed as one of many examples of insects controlled by the biopesticide.

U.S. Pat. Nos. 4,925,663; 5,683,689; 6,254,864; and 6,403,085 disclose a biopesticide effective against fire ants that includes the fungus *Beauveria bassiana*.

There remains a need for biocontrol and/or microbial control agents that eliminate or at least reduce the spread of fire ant colonies using novel pathogens. The present invention described below is directed to novel *Solenopsis invicta* viruses useful for the control of fire ants which are different from prior art pathogens and their uses.

SUMMARY OF THE INVENTION

It is therefore an object of the present invention to provide novel *Solenopsis invicta* virus (SINV) for biocontrol of *Solenopsis invicta*.

A further object of the present invention is to provide a nucleic acid sequence of SINV-1 for production of primers and biocontrol compositions.

A still further object of the present invention is to provide nucleic acid sequence SEQ ID NO 1.

Another object of the present invention is to provide nucleic acid sequence ID NO 21.

Another object of the present invention is to provide a biocontrol method for controlling fire ants that includes applying SINVs to a carrier that is a fire ant food source to form a biocontrol composition which is scattered near a fire ant colony.

Further objects and advantages of the present invention will become apparent from the following description.

BRIEF DESCRIPTION OF THE DRAWINGS

FIG. 1A is a drawing showing a schematic diagram of the *Solenopsis invicta* virus-1 (SINV-1) genome; open reading frames (ORFs) are shown in open boxes. Arrows represent approximate positions of nonstructural and structural proteins in ORFs 1 and 2, respectively.

FIG. 1B is a drawing showing a representation of the cloning strategy for the SINV-1 genome. Each line represents a cDNA fragment of the SINV-1 genome. The horizontal axis approximates corresponding positions in the genome diagram, p1, contiguous fragment obtained from the fire ant expression library; p2, 3'RACE; p3-p8, successive 5'RACE reactions.

FIGS. 2A-D are drawings showing comparisons of predicted amino acid sequences of nonstructural and structural proteins of SINV-1, picorna-like viruses, and viruses representative of the Picornaviridae and Cornoviridae. Alignments are of the conserved regions of the purtative helicase (A), Cysteine protease (B), RNA-dependent RNA polymerase (RdRp) (C), and capsid protein (D). The numbers on the left indicate the starting amino acids of the aligned sequences with the following SEQ ID NO's: SINC-123 (SEQ ID NO 40), ABPV 53 (SEQ ID NO 41), SBV 1369 (SEQ ID NO 42), BOCV 441 (SEQ ID NO 43), HAV 1219 (SEQ ED NO 45), SINV-1 663 (SEQ ID NO 46), ABPV 1166 (SEQ ID NO 47), SBV 2132 (SEQ ID NO 48), BOCV 904 (SEQ ID NO 49), CPMV 982 (SEQ ID NO 50), HAV 1558 (SEQ ID NO 51), SINV-1 1052 (SEQ ID NO 52), ABPV 1566 (SEQ ID NO 53), SBV 2522 (SEQ ID NO 54), BQMV 1317 (SEQ ID NO 55). CPMV 1357 (SEQ ID NO 56). HAV 1904 (SEQ ID NO 57), SINV-1 1184 (SEQ ID NO 58), ABPV 1700 (SEQ ID NO 59), SBV 2659 (SEQ ID NO 60), BOCV 1453 (SEQ ID NO 61), CPMV 1491 (SEQ ID NO 62), HAV 2035 (SEQ ID NO 63), SINV-1 704 (SEQ ID NO 64), ABPV 533 (SEQ ID NO 65), and BQCV 425 (SEQ ID NO 66). Identical residues in at least four of the six virus sequences are shown in reverse. Sequence motifs shown for the helicase (hel A, hel B, hel C) and RdRp (I-VII) correspond to those identified and reviewed by Koonin and Dolja (Crit. Rev. Biochem. Mol. Biol., Volume 28, 375-430, 1993). Asterisks above residues of the protease (B) correspond to the putative catalytic triad, which are considered essential for activity (Koonin and Dolja, 1993, supra; Ryan and Flint, J. Gen. Virol., Volume 78, 699-723, 1997). The last sequence shown (D) represents one of the conserved areas of the putative capsid protein region. The SINV-1 virus sequence exhibited greatest overall identity with acute bee paralysis virus.

Figure 8:
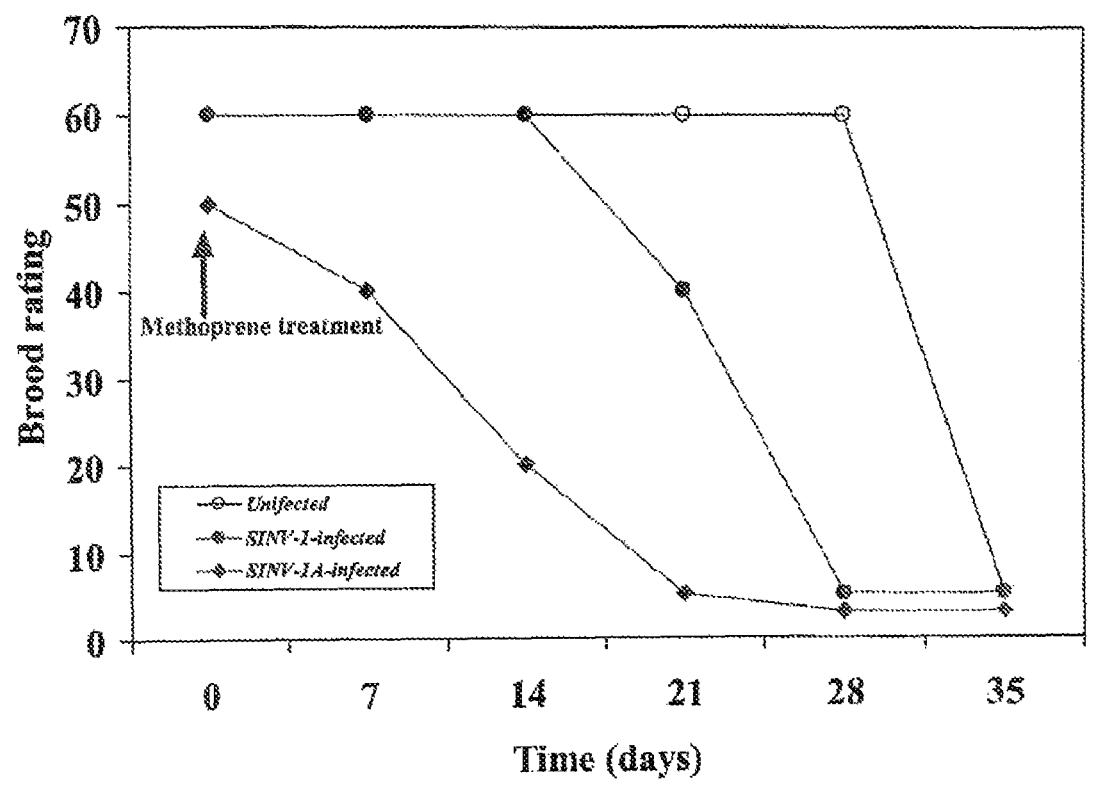

FIG. 8 is a graph showing the brood rating (ml) of *Solenopsis invicta* fire ant colonies 8, 9, and 17 over a 35-day period. Colonies 17 (♦) and 8 (●) exhibited sustained infections with SINV-1A and SINV-1 at the beginning of the experiment. Colony 9 (○) served as the control group. The up-arrow indicated the time at which each colony was treated with the insecticide, methoprene.

FIGS. 10A-10E show SEQ ID NO 1.

FIG. 11 shows the SINV-1A ORF-2 nucleic acid sequence SEQ ID NO 21.

FIG. 12 shows a cloned amplicon (SEQ ID NO 40) of SINV-1 infected fire ants from California that corresponds to a portion of the 3'-proximal open reading frame which encodes the structural proteins of the virus.

FIG. 13 shows a cloned amplicon (SEQ ID NO 41) of SINV-1 infected fire ants from Louisiana that corresponds to a portion of the 3'-proximal open reading frame which encodes the structural proteins of the virus.

FIG. 14 shows a cloned amplicon (SEQ ID NO 42) of SINV-1 infected fire ants from Oklahoma that corresponds to a portion of the 3'-proximal open reading frame which encodes the structural proteins of the virus.

FIG. 15 shows a cloned amplicon (SEQ ID NO 43) of SINV-1 infected fire ants from South Carolina that corresponds to a portion of the 3'-proximal open reading frame which encodes the structural proteins of the virus.

FIG. 16 shows a cloned amplicon (SEQ ID NO 44) of SINV-1 virus infected fire ants from Texas that corresponds to a portion of the 3'-proximal open reading frame which encodes the structural proteins of the virus.

FIG. 17 shows a cloned amplicon (SEQ ID NO 45) of SINV-1A infected fire ants from South Carolina that corresponds to a portion of the 3'-proximal open reading frame which encodes the structural proteins of the virus.

FIG. 18 shows a cloned amplicon (SEQ ID NO 46) of SINV-1A infected fire ants from Texas that corresponds to a portion of the 3'-proximal open reading frame which encodes the structural proteins of the virus.

DETAILED DESCRIPTION OF THE INVENTION

Figure 3:
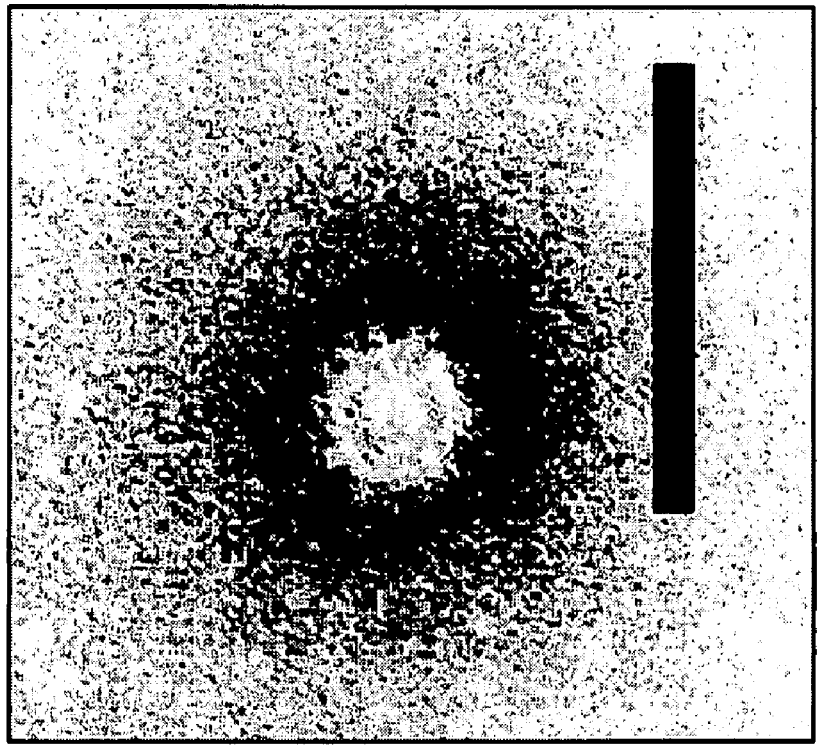
FIG. 3 is an electron micrograph of a particle believed to be SINV-1. The preparation was isolated from SINV-1-infected fire ants. Scale bar represents 100 nm.
Figure 3:
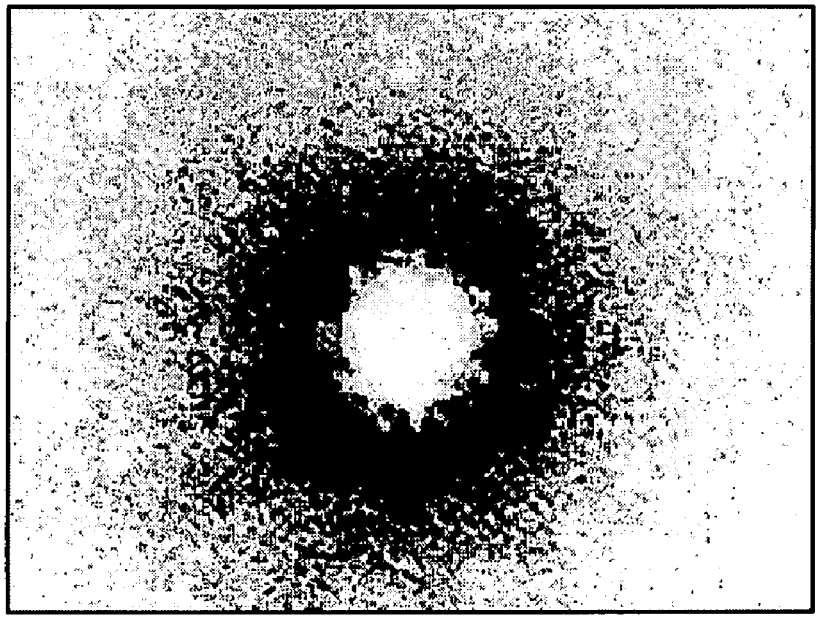

Although viruses can be important biological control agents against insect populations (Lacey et al., Biol. Comtemp., Volume 21, 230-248, 2001) none have been shown to infect *Solenopsis invicta*. The only report present in the literature was the observation of "virus-like particles" in a *Solenopsis* species from Brazil (Avery et al., Brazil, Fla. Entomol. Volume 60, 17-20, 1977). *Solenopsis invicta* viruses (SINV) represent the first infection of the red imported fire ant by this group of organisms. In the laboratory, SINV causes brood death of an entire colony and infection of healthy colonies (Valles et al., Virology, Volume 328, 151-157, 2004; Valles et al., J. Invert. Path., Volume 88, 232-237, 2005 both references herein incorporated in their entirety).

SINV particles are isometric with a diameter of about 31 nm. They have a monopartite, bicistronic, single-stranded RNA genome. To date, several SINV viruses have been isolated. SINV-1 is composed of about 8026 nucleotides. The genome size was confirmed by Northern analysis in which a band was observed at about 8.4 kb. ORFs 1 and 2 were found to be homologous to nonstructural and structural proteins, respectively, of well-characterized picorna-like viruses (Ghosh et al, J. Gen. Virol., Volume 80, 1541-1549, 1999; Govan et al., Virology, Volume 277, 457-463, 2000; Leat et al., J. Gen. Virol., Volume 81, 2111-2119, 2000).

Figure 2:
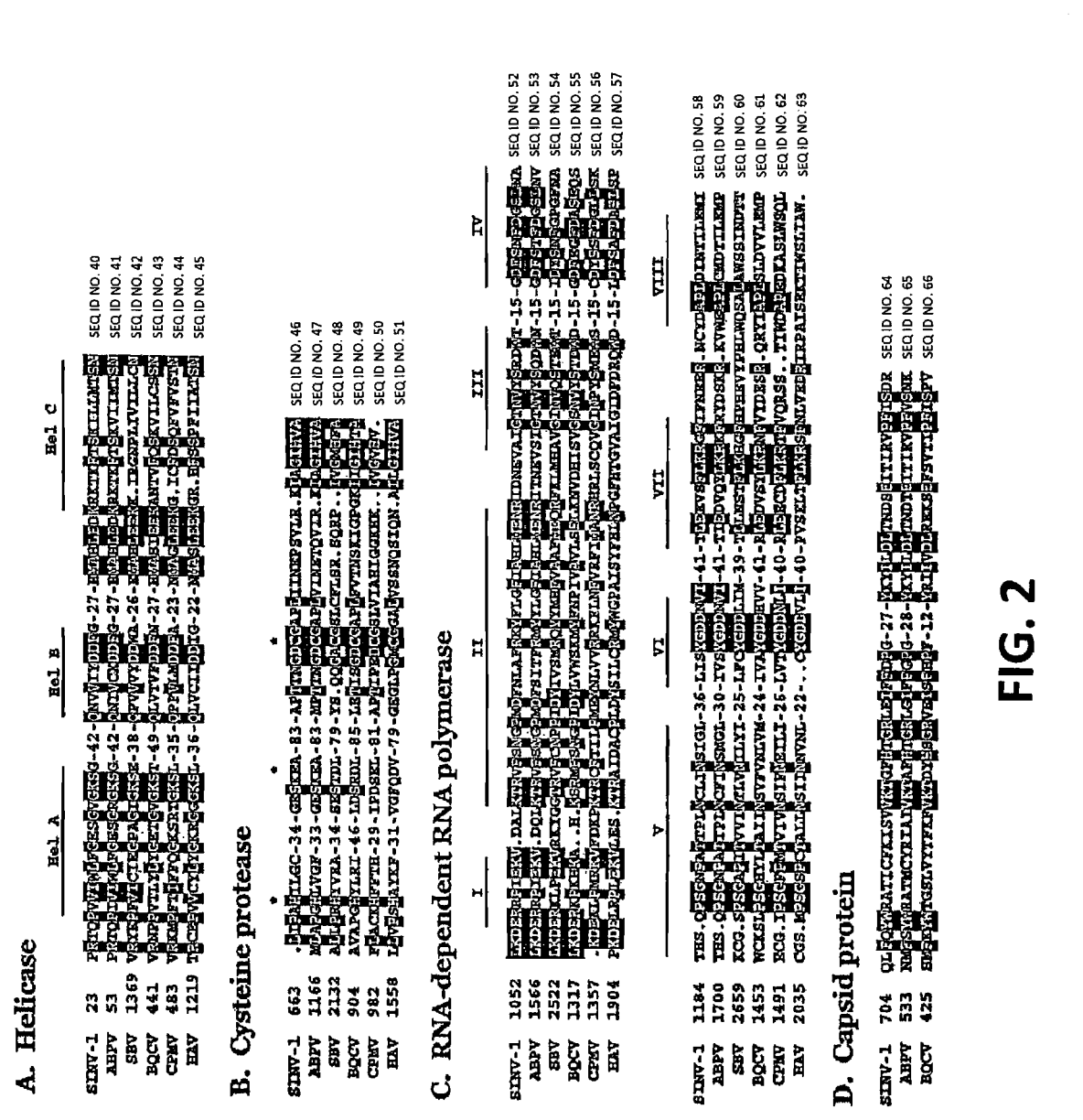

SINV-1 ORF-1 amino acid sequence was aligned with acute bee paralysis virus (ABPV), sacbrood virus (SBV), black queen cell virus (BQCV), cow pea mosaic virus (CPMV), and hepatitis A virus (HAV) using the Vecto NTI alignment software with ClustalW algorithm (InforMax, Inc. Bethesda, Md.)(FIGS. 2 and 10). Alignment of ORFs encoding nonstructural proteins with SINV-1 ORF 1 showed identities ranging from 10% (SBV, CPMV, HAV) to 30% (ABPV). The alignments also revealed sequence motifs for a helicase, protease, and RNA-dependent RNA polymerase (RdRp), characteristic of Picornaviridae, Cornoviridae, Sequiviridae, and Caliciviridae (Koonin and Dolja, Crit. Rev. Biochem. Mol. Biol., Volume 28, 375-430, 1993). Amino acid positions 23-144 exhibited similarity to the helicase. The consensus sequence for the RNA helicase, $Gx_4GK$ (Borbalenya et al., FEBS Lett., Volume 262 145-148, 1990), was found in the predicted ORF1 of SINV-1 at amino acids 34-40. Amino acids 663-823 showed similarity to the cysteine protease of picorna-, picorna-like-, sequi-, and comoviruses. Amino acids thought to form the catalytic triad of the protease, $H^{667}$, $E^{710}$, and $C^{802}$ were present in this region of the SINV-1 (Koonin and Dolja, 1993, supra; Ryan and Flint, J. Gen. Virol., Volume 78, 669-723, 1997). Furthermore, the consensus GxCG sequence motif was present at amino acids 800-803. Lastly, ORF1 of SINV-1 contained sequence with similarity to RdRp (amino acids 1052-1327). According to Koonin and Dolja (1993, supra) all-positive-strand RNA viruses encode the RdRp and comparative analysis revealed that they possess eight common sequence motifs (Koonin, J. Gen. Virol., Volume 72, 2197-2206, 1991). All eight of these motifs were present in SINV-1. Further, sequence motifs IV, V, and VI were reported to be unequivocally conserved throughout this class of viruses, exhibiting six invariant amino acid residues (Koonin and Dolja, 1993, supra). These "core" RdRp motifs were shown by site-directed mutagenesis to be crucial to the activity of the enzyme (Sankar and Porter, I. J. Biol. Chem., Volume 267, 10168-10176, 1992). The SINV-1 possesses all six of these characteristic residues, $D^{1130}$, $D^{1135}$ (motif IV), $G^{1190}$, $T^{1194}$ (motif V), and $D^{1248}$, $D^{1249}$ (motif VI). Thus, these data strongly support the conclusion that SINV-1 is a single-stranded positive RNA virus.

During elucidation of the genome of SINV-1, a nucleotide sequence, similar to but distinct from SINV-1, was discovered. The sequence, SINV-1A, is homologous to SINV-1 ORF 2, i.e., structural proteins, of picorna-like insect viruses with highly significant identity to SINV-1. This suggests that SINV-1A is a distinct, closely related species or a genotype of SINV-1 (FIG. 11 and SEQ ID NO 21).

SINV-1A is sufficiently similar to SINV-1 to occasionally result in amplification even in cases where oligonucleotide mismatches were present. SINV-1A is a compilation of contiguous fragments that do not match the SINV-1 sequence perfectly.

The nucleotide sequence of the 3'-end (structural proteins) of SINV-1 and SINV-1A exhibit about 89.9% nucleotide identity and about 97% amino acid identity of the translated 3' proximal ORF.

SINV-1 and SINV-1A infect S. invicta in the same geographic locations (sympatry). S. invicta has 2 distinct social forms, monogyne and polygyne, and these differences were shown recently to have a genetic basis (Krieger and Ross, Science, Volume 295, 328-322, 2002). Monogyne S. invicta is characterized as having a single fertile queen and polygyne S. invicta has multiple fertile queens. Both viruses infect both social forms. Dual infections with SINV-1 and SINV-1A were found in both monogyne and polygyne nests. Social form-specific pathogen infectivity has been reported previously in S. Invicta. Oi et al. (Environ. Entomol., Volume 33, 340-345, 2004) showed that infection of North American S. invicta with the microsporidian Thelohania solenopsis, was restricted to the polygyne social form.

Other SINV viruses have been discovered in fire ant colonies in California, Louisiana, South Carolina, Texas, and Florida. SEQ ID NOs 40-46 (FIGS. 12-18) represent cloned amplicons from these virus-infected ants. The cloned amplicons were generated with oligonucleotide primers p114 (SEQ ID NO 25) and p116 (SEQ ID NO 26) for SINV-1 and p117 (SEQ ID NO 27) and p118 (SEQ ID NO 28) for SINV-1A using RT-PCR. The areas amplified correspond to a portion of the 3'-proximal open reading frame which encodes the structural proteins of the virus. Each primer set is specific to each virus or genotype.

SINV-1 and SINV-1A were found to infect all fire ant castes. The viruses are transmissible by simply feeding uninfected ants a homogenate prepared from SINV-1- and/or SINV-1A-infected individuals. The viruses were present in field populations of S. invicta from several locations in Florida. Nests from some areas were devoid of infection, but in some locations infection rates were as high as about 88%.

The present invention provides nucleic acids encoding for SINV-1 as set forth in SEQ ID NO 1 (GenBank Accession NO. AY63414; herein incorporated by reference) and FIGS. 10A-10E. The invention also provides nucleic acid sequences (SEQ ID NO 2-20) capable of selectively hybridizing DNA, RNA, and cDNA sequences which can be derived from SEQ ID NO 1. To isolate SINV-1, RNA from fire ants, collected from a fire ant mound, was extracted from about 20-50 workers using TRIZOL reagent according to the manufacturer's directions (Invitrogen, Carlsbad, Calif.).

The present invention also provides a nucleic acid encoding ORF2 gene for SINV-1A as set forth in SEQ ID NO 21. The invention also provides nucleic sequences 2, 3 and 22-39 which are capable of selectively hybridizing DNA, RNA, and cDNA sequences which can be derived from SEQ ID NO 21.

The present invention further provides nucleic acid encoding 3'-proximal open reading frames for other SINV viruses infecting ants from other several different regions of the United States.

With the primers of the present invention, one of ordinary skill in the art could readily identify SINV viruses of the present invention.

For purposes of the present invention, the term "fire ant" and "Solenopsis invicta" are used interchangeably to describe the common red fire ant, originating in South America, but now commonly found in the United States, and Puerto Rico. The term fire ant also is used to describe black fire ants and other hybrid fire ants or other ants that are infected by the viruses of the present invention.

For purposes of the present invention, the term "isolated" is defined as separated from other viruses found in naturally occurring organisms.

For purposes of the present invention, the term "composition" is used to describe a composition which contains the virus of the presently claimed invention, optionally a carrier and optionally a pesticide. The carrier component can be a liquid or a solid material and is an inert, non-repellent carrier for delivering the composition to a desired site. Liquids suitable as carriers include water, and any liquid which will not affect the viability of the viruses the of present invention. Solid carriers can be anything which the fire ant will feed on. Non-limiting examples of solid carriers of the present invention include materials such as corn cob grits, extruded corn pellets, boiled egg yolks, and frozen insects such as crickets.

Optional toxicants include Chlorfenapyr, Imidacloprid, Fipronil, Hydramethylnon, Sulfluramid, Hexaflumuron, Pyriproxyfen, methoprene, lufenuron, dimilin, Chlorpyrifos, and their active derivatives, Neem, azadiractin, boric acid based, etc. The toxicant acts as a stressor which may be required to initiate viral replication which in turn results in brood death in the fire ant colony.

The term "effective amount" or "amount effective for" as used herein means that minimum amount of a virus composition needed to at least reduce, or substantially eradicate fire ants in a fire ant colony when compared to the same colony or other colony which is untreated. The precise amount needed will vary in accordance with the particular virus composition used; the colony to be treated; the environment in which the colony is located. The exact amount of virus composition needed can easily be determined by one having ordinary skill in the art given the teachings of the present specification. The examples herein show typical concentrations which will be needed to at least reduce the number of fire ants in a colony.

In the present method of using the viruses of the present invention, to reduce or eradicate a population of fire ants, the present compositions are delivered to the fire ant by spreading the composition at or near the fire ant colonies. The amount of composition used is an effective amount for producing the intended result, whether to reduce or eradicate the population of fire ants. The composition is prepared by homogenizing approximately 300 workers from an SINV infected colony in an equal volume of water and placing the resulting homogenate on a carrier.

The following examples are intended only to further illustrate the invention and are not intended to limit the scope of the invention as defined by the claims.

Example 1

A one-step reverse transcriptase polymerase chain reaction (RT-PCR) was used to identify SINV-1-infected *S. invicta* ants. A 20 ml scintillation vial was plunged into a fire ant mound in the field for several minutes to collect a sample of the worker caste. The ants were returned to the laboratory and RNA was extracted from about 20-50 workers using TRIZOL reagent according to the manufacturer's directions (Invitrogen, Carlsbad, Calif.) cDNA was synthesized and subsequently amplified using the One-Step RT-PCR kit (Invitrogen) with oligonucleotide primers p62-SEQ ID NO 25 and p63-SEQ ID NO 26 (Table 1). Samples were considered positive for the virus when a visible amplicon (about 327 nucleotides) was present after separation on about a 1.2% agarose gel stained with ethidium bromide. RT-PCR was conducted in a PTC 100 thermal cycler (MJ Research, Waltham, Mass.) under the following optimized temperature regime:

1 cycle at about 45° C., for about 30 minutes;
1 cycle at about 94° C. for about 2 minutes;
35 cycle at about 94° C. for about 15 seconds;
1 cycle at about 55° C. for about 15 seconds;
1 cycle at about 68° C. for about 30 seconds; and
a final elongation step of about 68° C. for about 5 minutes.

SINV-1 was purified for electron microscopy by the method described by Ghosh et al. (J. Gen. Virol., Volume 80, 1541-1549, 1999). Briefly, approximately 0.5 grams of a mixture of workers and brood were homogenized in about 5 ml of NT buffer (Tris-HCl, pH, about 7.4, approximately 10 mM NaCl) using a Potter-Elvehjem Teflon pestle and glass mortar. The mixture was clarified by centrifugation at about 1000×g for about 10 minutes in an L8-70M ultracentrifuge (Beckman, Palo Alto, Calif.) The supernatant was extracted with an equal volume of 1,1,2-trichlortrifluoroethane before the aqueous phase was layered onto a discontinuous CsCl gradient (about 1.2 and about 1.5 g/ml) which was centrifuged at about 270,000×g for about 1 hour in an SW60 rotor. Two whitish bands visible near the interface were removed by suction and desalted. The sample was negatively stained with about 2% phosphotungstic acid, about pH 7, and examined with a Hitachi H-600 transmission electron microscope (Hitachi, Pleasanton, Calif.) at an accelerating voltage of about 75 kV. Uninfected worker ants were prepared and examined in the same manner and served as controls.

A portion of the SINV-1 genome was identified from an expression library produced from a monogyne *S. invicta* colony collected in Gainesville, Fla. This contiguous 1780-nucleotide fragment exhibited significant identity with the acute bee paralysis virus and was comprised of clones 14D5, 3F6, and 24C10 (Table 2). From this fragment, a series of 5'RACE comprised of clones 14D5, 3F6, and 24C10 (Table 2). From this fragment, a series of 5'RACE reactions were conducted to obtain the upstream sequence of the SINV-1 genome using the 5'RACE system (Invitrogen). cDNA was synthesized with a gene-specific oligonucleotide primer (GSP) from total RNA, the RNA template was degraded with RNase, and the cDNA purified. The 3' end of the cDNA was polycytidylated with terminal deoxynucleotidyl transferase and dCTP. The tailed cDNA was then amplified with a second, upstream GSP and an abridged anchor primer.

Six 5' RACE reactions were necessary to obtain the entire SINV-1 genome. Anticipating the potential need to remove the VPg often covalently attached to the 5' end of insect picorna-like viruses (Christian and Scotti, In: The Insect Viruses, Plenum Publishing Corporation, New York, 301-336, 1998) 50 µg of total RNA prepared from SINV-1 infected ants was digested with about 609 µg/ml proteinase K for approximately 1 hour at about 37° C. The digested RNA was purified by acidic phenol/chloroform/isoamyl alcohol extraction. cDNA synthesis was conducted for about 50 minutes at about 45° C. with approximately 2.5 µg of total RNA using olignucleotide primers p134-SEQ ID NO 5, p138-SEQ ID NO 7, p138-SEQ ID NO 9, p175-SEQ SEQ ID NO 13, p162-SEQ ID NO 14, and p274-SEQ ID NO 20 (See FIG. 1B, p3 to p8), respectively. After cDNA synthesis, PCR was conducted with an abridged anchor primer and p135-SEQ ID NO 6, p140-SEQ NO 11, p154-SEQ ID NO 12, p161-SEQ ID NO 29, and p273-SEQ ID NO 19, respectively. PCR was conducted using the following temperature regime:

1 cycle at about 94° C. for about 2 minutes;
35 cycles of about 94° C. for about 15 seconds;
1 cycle at about 68° C. for about 5 minutes; and
followed by a final elongation step of about 68° C. for about 5 minutes.

Gel-purified amplicons were ligated into pCR4-TOPO vector, transformed into TOP10 competent cells (Invitrogen), and sequenced by the Interdisciplinary Center foe Biotechnology Research (University of Florida).

A single 3' RACE reaction was conducted with the Gene Racer kit (Invitrogen). cDNA was synthesized from about 1 µg total RNA purified from SINV-1-infected workers and brood using the GeneRacer Oligo dT primer p113-SEQ ID NO 4 and the GeneRacer 3' primer. Amplicons were closed and sequenced as described for the 5' RACE.

Northern analysis was conducted to determine the genome size following the general procedure of Sambrook and Russell (Molecular Cloning, Cold Spring Harbor Laboratory Press, Cold Spring Harbor, N.Y., 2001). Membranes were blotted with approximately 6 µg of total RNA from SINV-1-infected and -uninfected fire ant colonies, The approximately 327-nucleotide probe was synthesized using oligonucleotide primers p62-SEQ ID NO 2 and p63-SEQ ID NO 3 (Table 1) and a clone from the 3' end of the genome as template (Genomic region 6246 to 6572).

The genome of SINV-1 was constructed by compiling sequences from a series of six successive 5' RACE reactions, one 3' RACE reaction, and the sequences of three cDNA clones from a fire ant expression library (FIG. 1). The SINV-1 genome, SEQ ID NO 1, was found to be 8026-nucleotides long, excluding the poly(A) tail present on the 3' end (GenBank Accession number AY634314). This genome size was consistent with the largest species (approximately 8.4 kb) produced by Northern analysis of RNA extracted from SINV-1-infected fire ants (data not shown). No hybridization was observed in RNA extracted from uninfected ants.

Typical of Picornaviridae, the genome sequence was A/U rich (approximately 32.9% A, 28.2%, U, 18.3% C, and 20.5% G). Analysis of the genome revealed two large open reading frames (ORFs) in the sense orientation (within frame) with an untranslated region (UTR) at each end and between the two ORFs. The 5' proximal ORF (ORF1) commenced at the first start AUG codon present at nucleotide position 28 and ended at a UAA stop codon at nucleotide 4218, which encoded a predicted product of approximately 160,327 Da. The 3' proximal ORF (ORF2), commenced at nucleotide position 4390 (AUG start codon), terminated at nucleotide position 7803 (UAA stop codon), and encoded a predicted product of approximately 127,683 Da. No large ORFs were found in the inverse orientation, suggesting that the SINV-1 genome was a positive-strand RNA virus. The 5', 3', and intergenic UTRs were comprised of about 27, 223 and 171 nucleotides, respectively. BLAST analysis (Altschul et al., Nucleic Acids Research, Volume 25, 3389-3402, 1997) of ORFs 1 and 2 revealed identity to nonstructural and structural proteins, respectively, from picorna-like viruses. ORF1 of SINV-1 genome was found to exhibit the characteristic helicase, protease, and RNA-dependent RNA polymerase (RdRp) sequence motifs ascribed to Picornaviridae (FIG. 2; Koonin and Dolja, 1993, supra). Although ORF2 exhibited homology to structural proteins in the Picornaviridae, the sequence identity was less well conserved as in the nonstructural proteins of ORF1.

Electron microscopic examination of negatively stained samples from SINV-1-infected fire ants revealed particles that were consistent with Picornaviridae (FIG. 3). Isometric particles with a diameter of approximately 31 nm were observed exclusively in preparations from SINV-1-infected fire ants; no corresponding particles were observed in samples prepared from uninfected fire ants.

TABLE 1

Oligonucleotide primers

| Oligonucleotide Designation | Oligonucleotide (5'→3') |
|---|---|
| p62 | GGAAGTCATTACGTGGTCGAAAACG SEQ ID 2 |
| p63 | CGTCCTGTATGAAAACCGGTCTTTACCACAGAAA TCTTA SEQ ID NO 3 |
| p113 | GGAAGTCATTACGTGGTCGAAAAC SEQ ID NO 4 |
| p134 | CCAAGCTGCCCTTCATCTGCACCAGATC SEQ ID NO 5 |
| p135 | TTCATCTGCACCAGATCTCCAGGGCTC SEQ ID NO 6 |
| p136 | CAATGATTCAGCAGAAATGGTTATCC SEQ ID NO 7 |
| p137 | GTCACATCACGTCGGTGTCGT SEQ ID NO 8 |
| p138 | TCTGCCTTAAGTATTGATG SEQ ID NO 9 |

TABLE 1-continued

Oligonucleotide primers

| Oligonucleotide Designation | Oligonucleotide (5'→3') |
|---|---|
| p139 | GTCTCCTGGCAAGGAATACTGTCTGATGGCTGG SEQ ID NO 10 |
| p140 | GGAAGAGCGACGCGAGGTTGTTCAACATC SEQ ID NO 11 |
| p154 | CGCATCAACTTTCTCAATGGGTCGTCGCTCA SEQ ID NO 12 |
| p157 | CAGTGATACTAGCAATCTGAATA SEQ ID NO 13 |
| p162 | CTATCTAAATGTTGGGAATATC SEQ ID NO 14 |
| p164 | CACCGGATGTTGTGGCCTCCAGAATGAC SEQ ID NO 15 |
| p165 | AATGGAAGAAGACACTTCGATGTGGCACGACTC SEQ ID NO 16 |
| p177 | GAATCGTGCCACATCGAAGTGTCTTCTTCCATTG SEQ ID NO 17 |
| p180 | CATTGGGTTGGTTAAATATG SEQ ID NO 18 |
| p273 | CACAACTGGTTGGGTTCGAGGTTTG SEQ ID NO 19 |
| p274 | TGACTTACCTACGCCACTTTC SEQ ID NO 20 |

TABLE 2

Expression library clones exhibiting homology to viruses after BLAST analysis.

| Clone | BLAST Match | Accession no. | Score |
|---|---|---|---|
| 3B4 | Finkel-Biskis-Reilly murine Sarcoma virus | NP032016 | $3 \times 10^{-22}$ |
| 3F6 | Capsid protein, acute bee paralysis virus | AAL05914 | $1 \times 10^{-17}$ |
| 11F1 | Capsid polyprotein, *Drosophila* C Virus | NP044946 | $4 \times 10^{-16}$ |
| 12G12 | Noncapsid protein, Urochloa hoja blanca virus | AAB58302 | $5 \times 10^{-12}$ |
| 14D5 | Capsid protein, acute bee paralysis virus | AAK15543 | $1 \times 10^{-26}$ |
| 16A4 | Protein P1, *Acyrthosiphum pisum* virus | NP620557 | $5 \times 10^{-4}$ |
| 18F8 | Polyprotein, sacbrood virus | NP049374 | 5.9 |
| 24C10 | Capsid protein, acute bee paralysis virus | AAL05915 | $2 \times 10^{-13}$ |

Example 2

A field survey was conducted to examine the extend of SINV-1 infection among *S. invicta* nests from locations around Florida. Nests were samples from Gainesville (n=72), Newberry (n=11), LaCrosse (n=0), McIntosh (n=9), Fort Pierce (n=6), Orlando (n=4), Okahumpka (n=4), Ocala (n=4), Canoe Creek (n=4), Fort Drum (n=4), Cedar Key (n=11), Otter Creek (n=10), Bronson (n=9), and Perry (n=11). Samples of workers were retrieved from the field and treated as described above in Example 1. Primer pairs p62/p63 (SEQ ID NO 2/3), p136/p137 (SEQ ID NO 7/8), or p164/p165

(SEQ ID NO 15/16) were used in an RT-PCR reaction to determine the presence of SINV-1 infection (Table 1 above).

Experiments were conducted to determine if the virus was infection all caste members. Samples of workers were taken from ant nests from areas in Gainesville, Fla. and examined for infection by RT-PCR using primer pairs p62-SEQ ID No 2/63-SEQ ID NO 26, p136-SEQ ID NO 7/137-SEQ ID NO 8, or p164-SEQ ID NO 15/p165-SEQ ID NO 16 (Table 1 above and Table 4 below). Nests determined to be infected wee revisited on the same day, and samples of queens, workers, early instars ($1^{st}$ and $2^{nd}$), late instars ($3^{rd}$ and $4^{th}$), pupae, sexual pupae, and male and female alates were directly taken from the field. Queens were placed separately into 1.5 ml microcentrifuge tubes and held at about 30° C. for about 24 hours to obtain a sample of eggs. All samples were analyzed for infection by RT-PCR.

The PCR analytic survey for the SINV-1 virus from extracts of S. invicta collected around Florida revealed a pattern of fairly widespread distribution (Table 3). Among about 168 nests surveyed, infection rates among different sites ranged from about 0% to about 87.5% with a mean of about 22.9% (SD=26.3) infected. It appears that SINV-1 infects S. invicta year round in Florida because it was found from May to January. Although the rate of infection among individuals within SINV-1-infected nests was not determined, it was found that the infection was present in all caste members and developmental stages, including eggs, early (1st, $2^{nd}$) and late ($3^{rd}$-$4^{th}$) instars, worker pupae, workers, sexual pupae, alates (male and female) and queens (data not shown).

TABLE 3

Survey of fire ant nests for the presence of the fire ant virus (SINV-1).

| Date | Location (city, state) | Nests Surveyed | Nests with SINV-1 (%) |
|---|---|---|---|
| 14 May | Gainesville, FL | 10 | 20 |
| 12 June | Gainesville, FL | 10 | 30 |
| 21 July | Gainesville, FL | 16 | 87.5 |
| 18-30 September | Gainesville, FL | 28 | 14.3 |
| 7 October | Newberry, FL | 11 | 9.1 |
| 10 October | LaCrosse, FL | 9 | 0 |
| 16 October | McIntosh, FL | 9 | 44 |
| 23 December | Gainesville, FL | 8 | 75 |
| 14 January | Fort Pierce, FL | 6 | 0 |
| 14 January | Orlando, FL | 4 | 0 |
| 14 January | Okahumpka, FL | 4 | 25 |
| 14 January | Ocala, FL | 4 | 50 |
| 14 January | Canoe Creek, FL | 4 | 0 |
| 14 January | Fort Drum, FL | 4 | 0 |
| 22 January | Cedar Key, FL | 11 | 27 |
| 22 January | Otter Creek, FL | 10 | 0 |
| 22 January | Bronson, FL | 9 | 22 |
| 29 January | Perry, FL | 11 | 9.1 |

Example 3

To evaluate the transmissibility of the SINV-1, uninfected polygyne nests were identified by RT-PCR, excavated from the field, and parsed into two equivalent fragment colonies comprised of a queen, about 0.25 grams of brood, and about 0.5 grams of workers. Colonies were infected by the method described by Ackey and Beck (J. Insect Physiol., Volume 18, 1901-1914, 1972, herein incorporated by reference). Workers and brood, about 1-5 grams each from an SINV-1-infected colony, were homogenized in an equal volume of water and immediately placed onto boiled chicken egg yolks which are a food source for ants. The food source was placed into one of the fragment colonies for about 3 days. The control was identical except uninfected ants were used. Workers from treated and untreated paired fragment colonies were sampled at about 3, 11, and 18 days after introduction of the treated food source and analyzed for the SINV-1 by RT-PCR.

To determine the duration of SINV-1 infection within a fire ant colony, infected colonies were identified in the field, excavated, and placed into rearing trays with a food source of approximately 3 grams of cooked chicken egg yolks, approximately 15 frozen crickets, 10% sugar water, and a colony cell. Periodically, worker ants were removed and analyzed for infection by RT-PCR. Control colonies, without detectable SINV-1 infection, were removed from the field and treated as the infected colonies.

Individuals from uninfected colonies were infected within about 3 days of providing uninfected fire ants the food source mixed with a homogenate made from SINV-1 infected worker ants. SINV-1 did not appear to infect every individual within the region colonies; often several samples had to be evaluated by RT-PCR to detect infection. The infection was detectable for at least 18 days after treatment, indicating sustained infection among recipient colonies.

SINV-1 infection was detectable for at least about 3 months among colonies excavated from the field and held in the laboratory.

Example 4

A second nucleotide sequence, similar to SINV-1, was discovered during elucidation of the genome of SINV-1. To obtain cDNA of nucleotide sequence similar to but distinct from SINV-1, approximately 50 μg of total RNA prepared from SINV-1A-infected ants as in example 2 was digested with approximately 600 μg/ml proteinase K for about 1 hour at about 37° C. Fire ants were identified as being infected with SINV-1A with oligonucleotide primers p117 and p118 (Seq. ID nos. 29 and 30). The digested RNA was purified by acidic penol:chloroform:isoamyl alcohol extraction. One-step RT-PCR (Invitrogen) was conducted with primer pairs p62-SEQ ID NO 2 p63-SEQ ID NO 3, p102-SEQ ID NO 24, p191-SEQ ID NO 33; p59-SEQ ID NO 23, p221-SEQ ID NO 35; p188-SEQ ID NO 30 p222-SEQ ID NO 36, p188-SEQ ID NO 30, p189-SEQ ID NO 31, p137-SEQ ID NO 8, and p193-SEQ ID NO 34 (Table 4) using the following temperature regime:

Reverse transcriptase at about 45° C. for abut 50 minutes
Denaturation at about 94° C. for about 2 minutes
35 cycles of denaturation at about 94° C. for about 15 seconds
Annealing (for individual temperatures see Table X) for about 15 minutes, and
Elongation at about 68° C. for out 1.5 minutes
Final elongation at about 68° C. for about 5 minutes Gel purified amplicons were ligated in to the pCR4-TOPO vector and transformed into TOP10 competent cells (Invitrogen). Insert-positive clones were sequenced by the Interdisciplinary Center for Biotechnology Research University of Florida.

A single 3' RACE reaction was conducted with the GeneRacer kit (Invitrogen). cDNA was synthesized from approximately 1 μg total RNA purified from SINV-1A-infected workers and brood using the GeneRacer Oligo(dt) primer. The cDNA was amplified by PCR with oligonucleotide primer p58-SEQ ID NO 22 or p114-SEQ ID NO 25 and the GeneRacer 3'primer. Amplicons were cloned and sequenced as described above.

BLAST comparisons of the nucleotide sequence and predicted amino acid sequence of the 3-proximal ORF and Clustal W-based algorithm alignments were conducted using the Vector NTI alignment software (InforMax, Bethesda, Md.).

The 3'-end of the genome of SINV-1A was constructed by compiling sequences from a series of RT-PCRs and a 3'RACE reaction. The sequence was about 2845 nucleotides in length, excluding the poly(A) tail present on the 3'-end (Accession No. AY831776) (SEQ ID NO 21). The nucleotide sequence was comprised of about 31.7% A, 28.6% U, 17.6% C and 22.1% G. Analysis of the nucleotide sequence revealed one large ORF in the sense orientation with untranslated regions (UTRs) of about 160 and 225 nucleotides at the 5' and 3' ends, respectively. Translations of the ORF commenced at nucleotide position 2620 (UAA stop codon), and encoded a predicted product of approximately 92,076 Da. When the SINV-1 and SINV-1A sequences were compared, the start signal in SINV-1 was further upstream and the corresponding ORF larger compared with SINV-1A. Because the sequences of SINV-1 and SINV-1A were so similar, it is likely that the start site could actually be are internal methoinine and the ORF site begins somewhere further upstream. No large ORFs were found in the inverse orientation. BLAST analyses (Altschul et al., Nucleic Acids Res., Volume 25, 3389-3402, 1997) of the translated ORF revealed identity to structural proteins from picorna-like viruses. The amino acid sequence was most identical to SINV-1 (97%), followed by the Kashmir bee virus (KBV, 30%), and acute bee paralysis virus (ABPV, 29%) (Table 5).

TABLE 4

Oligonucleotide primers and their annealing temperatures.

| Designation | Oligonucleotide 5' > 3' |
|---|---|
| p58 | GCGATAGGTTAGCTTTAAGTACAATTGGTG SEQ ID NO 22 |
| p59 | TCCCAATGTGCAATAAACACCTTCA SEQ ID NO 23 |
| p62 | GGAAGTCATTACGTGGTCGAAAACG SEQ ID NO 2 |
| p63 | CGTCCTGTATGAAAACCGGTCTTTACCACAGAAATCTTA SEQ ID NO 3 |
| p102 | CGCCTTAGGATTCGTTAGATACTCACCCG SEQ ID NO 24 |
| p114 | CTTGATCGGGCAGGACAAATTC SEQ ID NO 25 |
| p116 | GAACGCTGATAACCAATGAGCC SEQ ID NO 26 |
| p117 | CACTCCATACAACATTTGTAATAAAGATTTAATT SEQ ID NO 27 |
| p118 | CCAATACTGAAACAACTGAGACACG SEQ ID NO 28 |
| p137 | GTCACATCACGTCGGTGTCGT SEQ ID NO 8 |
| p161 | GCGCGTGAATAAGATGACATTGCTTCCGAATCTG SEQ ID NO 29 |
| p188 | CTTAATTGTAATTTACTTGAATATGCGTTTGC SEQ ID NO 30 |

TABLE 4-continued

Oligonucleotide primers and their annealing temperatures.

| Designation | Oligonucleotide 5' > 3' |
|---|---|
| p189 | GTATCTAACGAATCCTAAGGCGGATTG SEQ ID NO 31 |
| p190 | CAATCCGCCTTAGGATTCGTTAGATAC SEQ ID NO 32 |
| p191 | CGGATCTTATGAGTGAAGACACACCAG SEQ ID NO 33 |
| p193 | CAACCTCTGCTTCCCACGCAC SEQ ID NO 34 |
| p221 | GATGGTCTCGACCAAATGATATGGAG SEQ ID NO 35 |
| p222 | ATGAAGATATGAAGGTGTTTATTGCACATTG SEQ ID NO 36 |
| p341 | CACATAAGGGATATTGTCCCCATG SEQ ID NO 37 |
| p343 | TGGACGAGACGGATCTTATGAGTG SEQ ID NO 38 |
| 3' Primer | GCTGTCAACGATACGCTACGTAACG SEQ ID NO 39 |

TABLE 5

Comparative identities of SINV-1A amino acid sequences with corresponding sequences form other positive strand RNA viruses.

| Virus | Identity (%) | Accession No. |
|---|---|---|
| Solenopsis invicta virus 1 | 97.4 | AY634314 |
| Kashmir bee virus | 30.0 | NC004807 |
| Acute bee paralysis virus | 28.5 | NC002548 |
| Drosophila C virus | 16.2 | NC001834 |
| Triatoma virus | 14.8 | NC003783 |
| Black queen cell virus | 14.5 | NC003784 |
| Sacbrood virus | 12.1 | NC002066 |
| Hepatitis A virus | 11.7 | NC001489 |
| Cow-pea mosaic virus | 10.3 | NC003550 |

Example 5

A field survey was conducted to examine the extent of SINV-1 and SINV-1A infection and co-infection among *S. invicta* nests from four locations around Gainesville, Fla. Ten nests were sampled from 4 different areas in Gainesville (n=40, Table 2). One-step RT-PCR with species/genotype-specific oligonucleotide primers was used to identify virus-infected *S. invicta* nests. Samples of worker caste ants were collected as described above in Example 1. RNA was extracted from about 20-50 workers using Trizol reagent according to manufacturer's instructions (Invitrogen). cDNA was synthesized and subsequently amplified using the One-Step RT-PCR kit (Invitrogen) with oligonucleotide primers p117-SEQ ID NO 27 and p118-SEQ ID NO 28 (SINV-1A specific) and p114-SEQ ID NO 25 and p116-SEQ ID NO 26 (SINV-1 specific) (Table 4). Samples were considered positive for each virus when a visible amplicon of anticipated size (about 646 for nt for SINV-1 and about 157 nt for SINV-1A) was present after separation on about a 1.2% agarose gel stained with ethidium bromide RT-PCR was conducted in a PTC 100 thermal cycler (MJ Research, Waltham, Mass.) under the following optimized temperature regime:

1 cycle at about 45° C. for about 30 minutes
    1 cycle at about 94° C. for about 2 minutes
    35 cycles at about 94° C. for about 15 seconds
    1 cycle at about 54° C. for about 15 seconds
    1 cycle at about 68° C. for about 30 seconds
    Elongation step at about 68° C. for about 5 minutes In an attempt to gain additional insight into whether SINV-1A was a genotype or distinct species, oligonucleotide primers were designed to conserved areas, i.e., in common) of the 3'-end of the SINV-1 and SINV-1A sequences (p341-SEQ ID NO 37 and p343-SEQ ID NO 38, Table 4). These common primers were used for RT-PCR with representative ant colonies infected exclusively with either SINV-1 or SINV-1A (n=3); the resulting amplicons were subjected to analysis. Amplicons generated with the common primers from SINV-1 and SINV-1A-infected ant colonies were digested separately with AvaI and BglII, separated on about a 1.2% agarose gel and visualized by ethidium bromide staining.

In addition, colonies identified as being negative, i.e., no amplification, for infection by either SINV-1 or SINV-1A, as determined previously by RT-PCR and virus-specific primers, were subjected to a second RT-PCR with the common primers p341-SEQ ID NO 37 and p343-SEQ ID NO 38 (Table 4) to possibly identify additional species or genotypes.

A separate survey of monogyne and polygyne ants was conducted to determine if there was a social form-specific virus/genotype. Ant samples were taken from suspected monogyne- and and polygyne-predominant areas and evaluated for infection with SINV-1 and SINV-1A as described above in this example. These samples were concomitantly evaluated by PCR to determine the social form of the nest. Social form was determined with PCR by exploiting nucleotide differences between the 2 gp-9 alleles: Gp-$9^B$, Gp-$9^b$, found in North America S. invicta (Krieger and Ross, Science, Volume 295, 328-323, 2002) by the method described by Valles and Porter (Insect. Soc., Volume 50, 199-200, 2003; herein incorporated by reference).

An RT-PCR-based survey for SINV-1 and SINV-1A using RNA extracts of S. invicta collected around Gainesville, Fla., revealed a mean colony infestation rate of about 25% by SINV-1 and about 55% by SINV-1A (Table 6). Among 40 nests surveyed, infection rates among the four different sites ranged from about 10-40% for SINV-1 and about 40-70% for SINV-1A (Table 6). Both SINV-1 and SINV-1A were found to co-infect about 17.5% of the nests surveyed. It was not determined if individual ants were infected with both SINV-1 and SINV-1A.

Figure 4A:
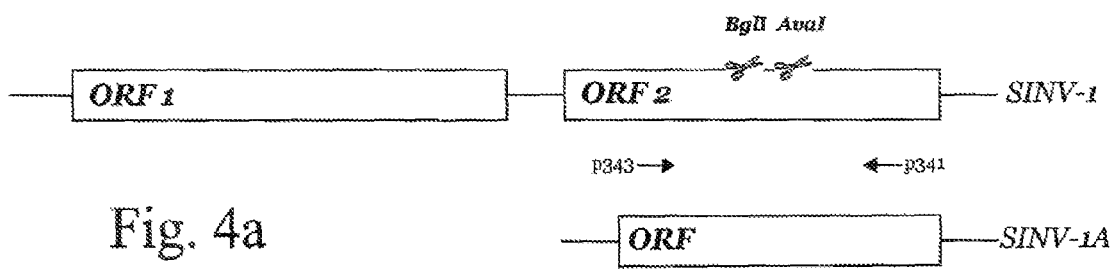
FIG. 4A is a schematic diagram of SINV-1 and SINV-1A genomes. ORFs are shown in open boxes. Conserved oligonucleotide primer positions are indicated by p341 and p343. Restriction positions unique to SINV-1 are approximated with scissor symbols.
Figure 4B:
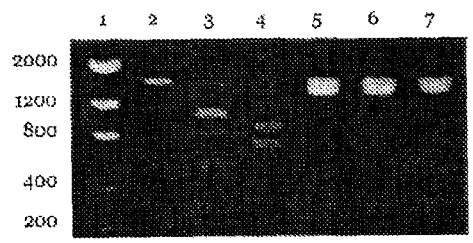
FIG. 4B is a photograph showing restriction fragment length polymorphism (RFLP) of a portion of the SINV-1 and SINV-1A genomes amplified with primers p341 and p343 and restriction digested with AvaI and BglII. Lane assignments are as follows: Land 1: molecular weight markers; Lane 2: SINV-1 undigested; Lane 3: SINV-1 AvaI-digested; Lane 4: SINV-1 BglII-digested; Lane 5: SINV-1A undigested; Lane 6: SINV-1A AvaI-digested; and Lane 7: SINV-1A BglII-digested.

RFLP analysis of about a 1584 nucleotide amplicon at the 3'-end of genomes produced with primers p341 (SEQ ID NO 37) and p343 (SEQ ID NO 38) form SINV-1 and SINV-1A-infected fire ants corroborated sequence data assembled for each species/genotype (FIG. 4). Digestion of this amplicon from SINV-1 infected fire ants with AvaI and BglII produced bands of approximately 550 and 1030 and 710 and 870 nucleotides in length, respectively. Conversely, the corresponding amplicon from SINV-1A-infected fire ants was not cut by either AvaI or BglII. All three replicates from different colonies of fire ant produced the same banding patterns and no amplicons were produced from uninfected ants.

RNA from colonies yielding no amplicon when utilizing SINV-1- and SINV-1A-specific primers, i.e., uninfected, was subsequently used with conserved primers (p341-SEQ ID NO 37 and p343-SEQ ID NO 38) in RT-PCR to possibly identify new viruses or genotypes related to SINV-1 and SINV-1A. In every instance (n=15), no amplification was observed with conserved primers.

SINV-1 and SINV-1A were found in monogyne and polygyne nests. Infection by either virus does not appear to be limited to a specific social form (Data not shown).

TABLE 6

Field Survey results of SINV-1 and SINV-1A infection of S. invicta from locations in Gainesville, Florida.

| Location(latitude/longitude) | SINV-1 infection(%) | SINV-1A infection(%) | Co-infection (%) |
|---|---|---|---|
| N29° 35.342', W082° 20.332' | 20 | 50 | 10 |
| N29° 45.824' W082° 24.352' | 30 | 40 | 20 |
| N29° 39.1' W082° 15.6' | 40 | 70 | 40 |
| N29° 40.128' W082° 31.395' | 10 | 60 | 0 |

Example 7

To evaluate the efficacy of Solenopsis invicta virus complex (SINV-1 and genotypes), uninfected monogyne nests (n=6) initiated by newly mated queens were identified by RT-PCR with oligonucleotide primers designed to the 2 characterized genotypes:

SEQ ID NO 25
p114 5'CTTGATCGGGCAGGACAAATTC

SEQ ID NO 26
p116 5'GAACGCTGATAACCAATGAGCC

SEQ ID NO 27
p117 5'CACTCCATACAACATTTGTAATAAAGATTTAATT

SEQ ID NO 28
p118 5'CCAATACTGAAACAACTGAGACACG

RT-PCR was conducted in a PTC 100 thermal cycler (MJ Research, Waltham, Mass.) under the following optimized temperature regime:

1 cycle at about 45° C. for about 30 minutes
    1 cycle at about 94° C. for about 2 minutes
    35 cycles at about 94° C. for about 15 seconds
    1 cycle at about 54° C. for about 15 seconds
    1 cycle at about 68° C. for about 35 seconds
    Elongation step at about 68° C. for about 15 minutes.

The colonies were comprised of about 40-60 ml of brood, about 40,000-60,000 workers, and a single inseminated queen. Three colonies were used as control and 3 colonies were treated with virus-infected ants. Each colony was randomly assigned and paired. Colonies were infected as described above in Example 4. Approximately 300 workers from an SINV-infected colony were homogenized in an equal volume of water and immediately placed onto a mixture of approximately 3 grams of boiled chicken egg yolks and approximately 15 frozen crickets. The control colonies were treated similarly except uninfected ants were used. About 30 workers from treated and control colonies were removed periodically and tested for known SINV genotypes by RT-PCR. Concomitantly, the colonies were quantitatively assessed by determining the volume of brood and number of workers using a standard rating method described previously (banks et al., J. Econ. Entomol., Volume 81, 83-87, 1988; herein incorporated by reference).

Figure 5:
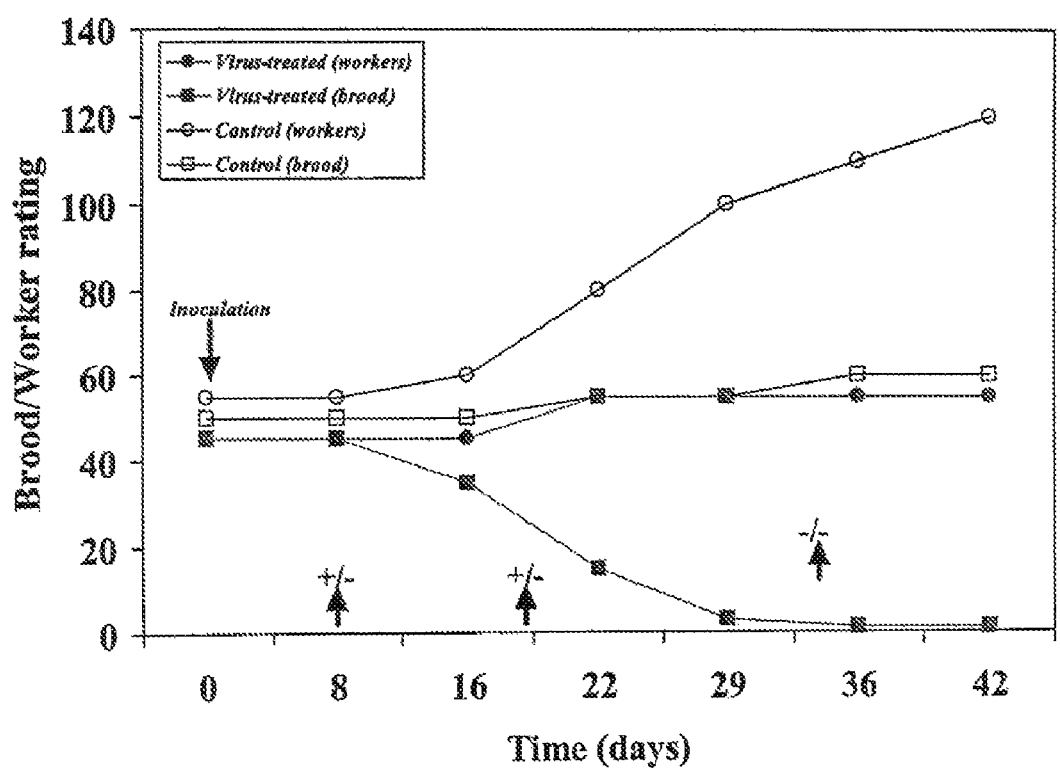
FIG. 5 is graph showing the brood rating (ml) and worker rating (×10³) of *Solenopsis invicta* fire ant colonies 10 and 14 over about a 42 day period. Colony 10 (red lines) was inoculated with *Solenopsis invicta* virus on day 0. Up-arrows indicate time points at which viral detection was assessed in each colony (treated and control) and the corresponding +/− symbols indicate positive and negative viral detection, respectively.
Figure 6:
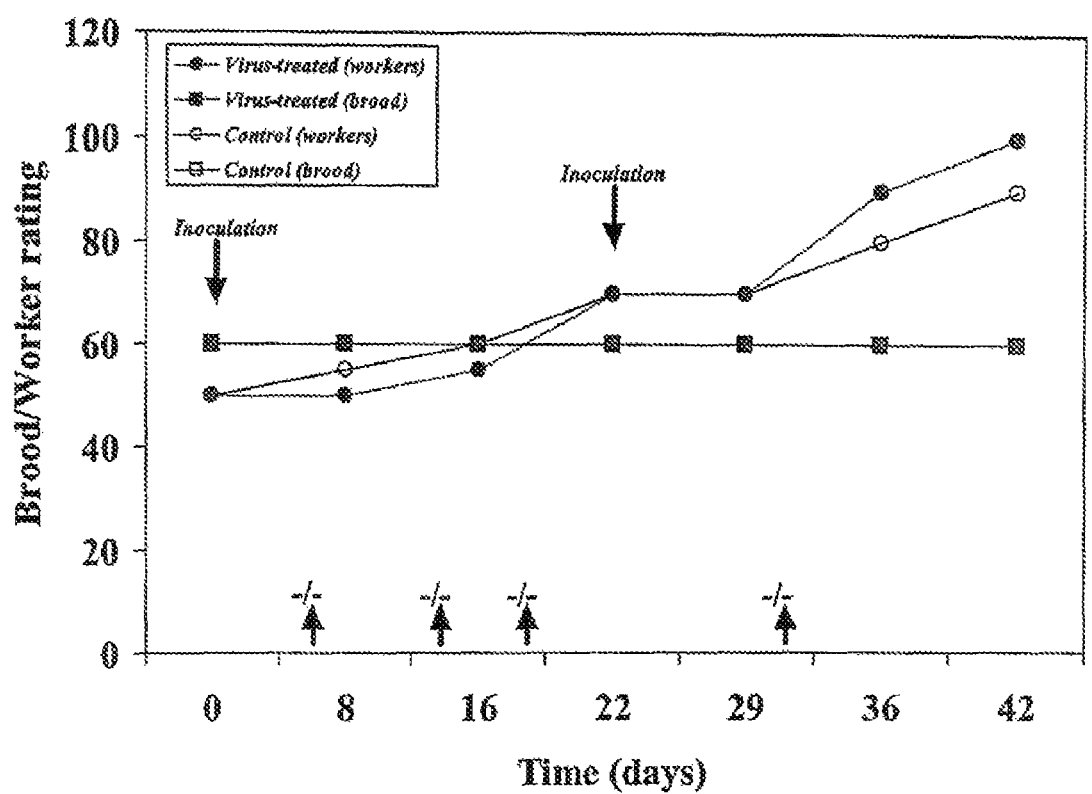
FIG. 6 is a graph showing the brood rating (ml) and worker rating (×10³) of *Solenopsis invicta* fire ant colonies 12 and 13 over a 42-day period. Colony 12 was inoculated with *Solenopsis invicta* virus on day 0. Up arrows indicate time points at which viral detection was assessed in each colony) treated and control) and the corresponding +/− symbols indicate positive and negative viral detection, respectively.
Figure 7:
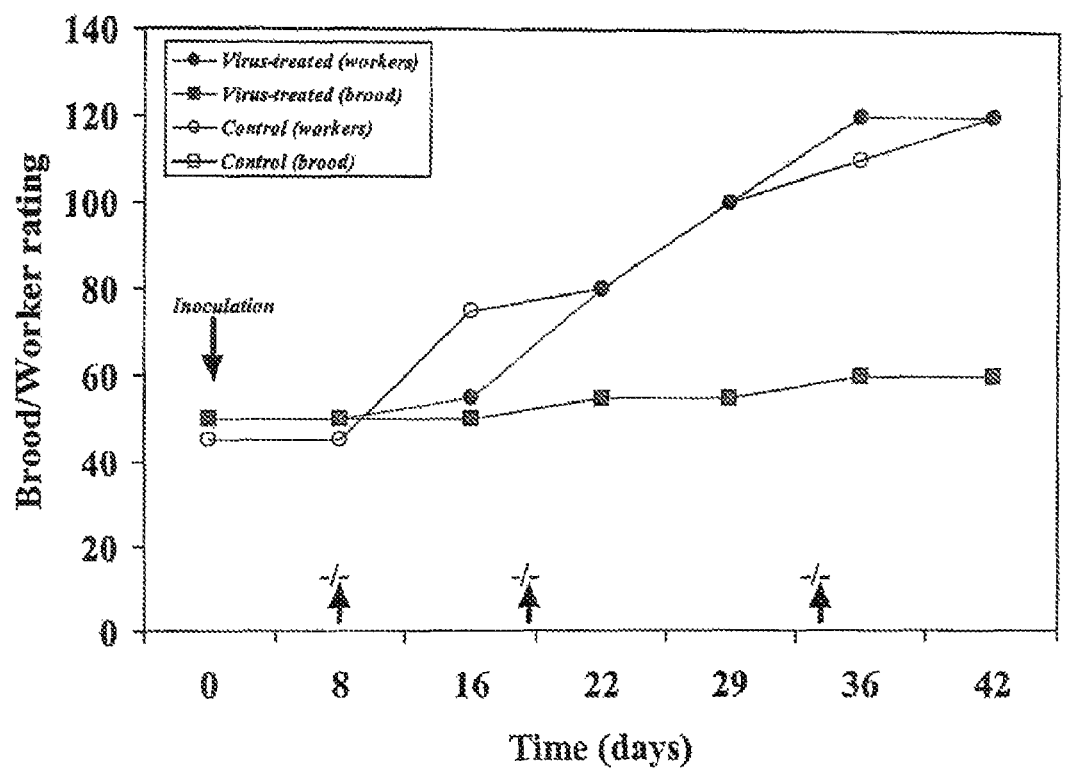
FIG. 7 is a graph showing the brood rating (ml) and worker rating (×10³) of *Solenopsis invicta* fire ant colonies 3 and 6 over a 42-day period. Up arrows indicate time points at which viral detection was assessed in each colony) treated and control) and the corresponding +/− symbols indicate positive and negative viral detection, respectively.
Figure 9:
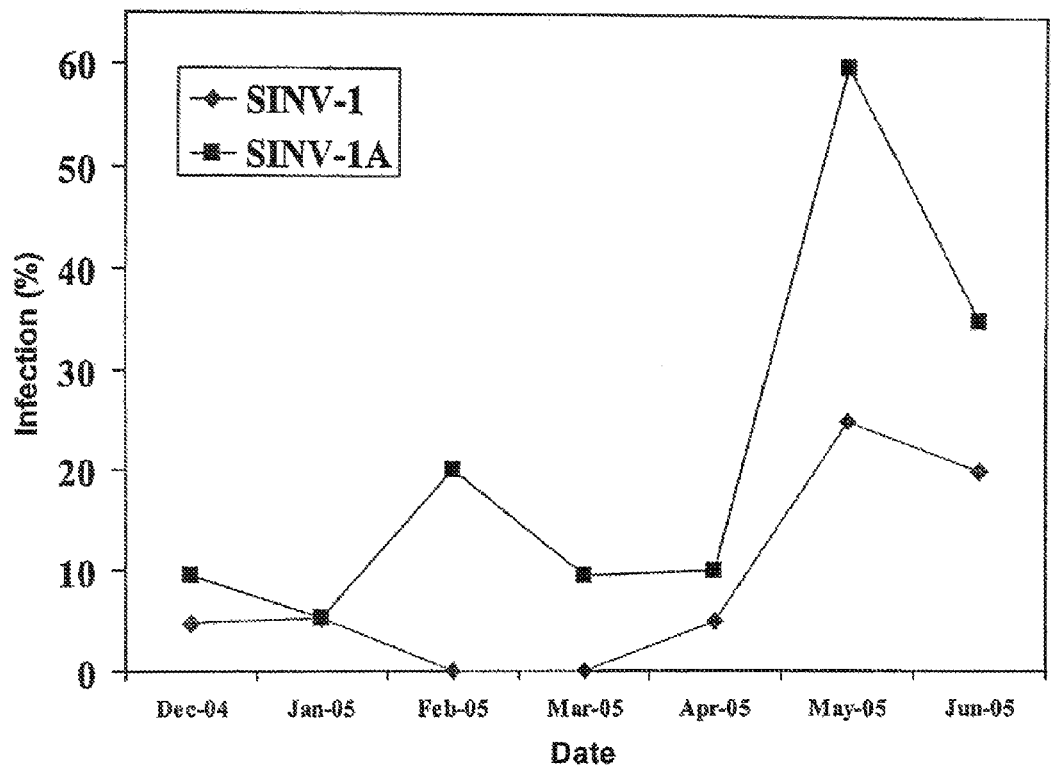
FIG. 9 is a graph showing the prevalence of SINV-1 and SINV-1A in *Solenopsis invicta* fire ant colonies sampled from two field locations in Gainesville. Fla.

FIGS. 5-7 illustrate the transmission and efficacy results. Three of the six colonies were inoculated with the virus at day 0 of the experiment as indicated. Viral transmission was successful in about 67% of the treatments (Colonies 10 and 12, FIGS. 5 and 6, respectively). The infection sustained itself in colony 10 for at least about 2 weeks (FIG. 5) and was associated with a precipitous and significant decline in brood. The brood rating in colony 10 declined from about 45 ml to less than 3 ml in about 28 days. Colony 10 never recovered and lingered with only adult ants over subsequent months. Fire ant colonies cannot survive without brood because all digestion of solid food is done by the fourth instars. Therefore, once the brood was killed off, the colony could never recover. The brood rating for the corresponding control colony 14 increased slightly over the same period as is observed in normal, healthy laboratory colonies.

Colony 12 (FIG. 6) appeared to be infected for about 2 consecutive weeks. However, the infection did not sustain itself in the population and possibly never achieved replication. The results from Colony 12 corroborate the conclusion that sustained viral infection and most likely replication was responsible for the decline and ultimate death of Colony 10 (FIG. 5). A second inoculation attempt was made against Colony 12 on day 22 but viral transmission did not occur (FIG. 7). Colony 3 remained as healthy as the control Colony 6.

Immune response of the ants must be considered when interpreting these results. Some ants, as any organism, are going to be more susceptible to infection and detrimental effects of a pathogen such as SINV than others. A range of susceptibility would be anticipated. Therefore, not all colonies would be expected to become infected when challenged. Moreover, previous exposure to similar pathogens, such as Cripaviruses, can provide protection to an insect challenged by a similar pathogen later.

Example 8

External stressors may be required to initiate replication of virus and result in brood death. To test this, 2 newly-mated queen colonies with brood ratings of about 50-60 ml, were infected with SINV-1 or SINV-1A. The virus-infected colonies and one control colony were treated with approximately 15 grams of Extinguish commercial formulation of methoprene (Wellmark, Schaumburg, Ill.) provided in a plastic weigh boat and monitored for about 35 days. Brood and worker ratings were assessed every 7 days after treatment by the method of Banks et al (1998, supra).

Brood were killed 1-3 weeks faster in two SINV-infected colonies treated with Methoprene than in an uninfected colony (FIG. 8). Note that among two SINV-infected colonies treated with methoprene, brood began dying in as little as about one week after treatment while no effects were detected in the uninfected colony for about four weeks.

Example 9

In order to understand effects of SINV against *Solenopsis invicta* in the field, two sites in Gainesville, Fla., were monitored for 7 months for SINV prevalence. One site was located on US441 on the north side of Paines Prairie State Preserve. The other site was located at the East University Avenue/SR26 junction. Ten fire ant nests from each site per month were sampled as described in Example 1 and used in subsequent RT-PCR analyses as described above in Example 7. Simple observation was used to characterize the mound density each month.

FIG. 9 illustrates the seasonal prevalence or phenology of the characterized genotypes, SINV-1 and SINV-1A. The prevalence of the virus remained fairly constant, averaging between 0% and about 60% during the winter and early spring months (December to April). However, a sharp increase in viral prevalence to about 60% for SINV-1A and about 28% for SINV-1 was observed in May. The fire ant nest density was reduced by approximately 50% in June as compared to May immediately following the spike in viral prevalence that occurred in May.

The foregoing detailed description is for the purpose of illustration. Such detail is solely for that purpose and those skilled in the art can make variations without departing from the spirit and scope of the invention.

We claim:

1. A *Solenopsis invicta* virus identifiable by a primer selected from the group consisting of SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ED NO 31, SEQ ID NO 32, SEQ ID NO 33, SEQ ID NO 34, SEQ ID NO 35, SEQ ID NO 36, SEQ ID NO 37, SEQ ID NO 38, and mixtures thereof.

2. A biocontrol composition comprising:
   a. an effective amount of a *Solenopsis invicta* virus of claim 1 to at least reduce the number of fire ants in a colony, and
   b. a carrier.

3. The composition of claim 2 wherein said carrier is a food source of said ants.

4. The composition of claim 3 wherein said food source is selected from the group consisting of insects, cooked egg yolk, corn cob grits, soybean oil, extruded corn pellets, and mixtures thereof.

* * * * *

SEQUENCE LISTING

```
<160> NUMBER OF SEQ ID NOS: 66

<210> SEQ ID NO 1
<211> LENGTH: 8026
<212> TYPE: DNA
<213> ORGANISM: Solenopsis Invicta Virus
<300> PUBLICATION INFORMATION:
<301> AUTHORS: Steven M. Valles et al.
<302> TITLE: A picorna-like virus from the red imported fire ant,
      Solenopsis invicta: initial discovery, genome sequence, and
      characterization
<303> JOURNAL: Virology
<304> VOLUME: 328
<306> PAGES: 151-157
<307> DATE: 2004-08-21
<300> PUBLICATION INFORMATION:
<308> DATABASE ACCESSION NUMBER: GenBank/AY634314
<309> DATABASE ENTRY DATE: 2004-09-29
<313> RELEVANT RESIDUES IN SEQ ID NO: (28)..(4218)
<300> PUBLICATION INFORMATION:
<308> DATABASE ACCESSION NUMBER: GenBank/AY634314
<309> DATABASE ENTRY DATE: 2004-09-29
<313> RELEVANT RESIDUES IN SEQ ID NO: (4390)..(7803)
```

<400> SEQUENCE: 1

```
catcgagatc tattgctacc cttccaaatg catatgaagt tgttggctga cttggttaag      60
atggttgata cctcaggcgc atttgggacc aaacctcgaa cccaaccagt tgtgatttgg    120
ttgtttggtg aaagtggcgt aggtaagtca ggcatgtcct ggcccctagc cattgatctg    180
aataatattt tcatgacaaa taaggaagat gcccggaact tctcgcgcaa catatatatg    240
cgaaatgttg agcaggagtt tgggacaat tatcaaggac aaaacgtagt tatatatgat     300
gattttggac aacgcaaaga ttcccaagca aaacccaacg aagaattcat ggaattgatt    360
cgtacagcta acatcgctcc atatccttta catatggcac atttagaaga taaacgaaag    420
actaaattta catcaaaaat tctacttatg acatccaacg tttttgaaca gagtgtagat    480
tctttaacct ttcctgatgc tttccgtagg cgcattgacc tgtgtggtcg cgtgtccaat    540
aaaccacaat ttaccaaacc aggttttttca aaagcaactg gtcaaactgt taaaagattg   600
gacaaagata gggttagaaa agaattcaat caagttattt caacagacgt ttatttaata    660
gatttaattg acgcagagac tggtgatgtc attgaagaag gattggatta tgcagaattc    720
ctagaacgag caacacagaa aactaacgaa gcattcaatc aatccgtaga attaaatgaa    780
tttttagaga attatgcaga atcccgatat cgactagcaa caatgcaggt aggcgatgaa    840
tttcatgact gtaataattt attacttatt aagatagaaa actttgatga tttacctagc    900
aatacgcttt tatttgattc acaaggaaat tccaaatcta acgagaaat tgaggaaaat     960
ttacagaatg catgggtggc aatggaagaa gacacttcga tgtggcacga ttcttattat   1020
aattttagag atgacatagt gtataaaaag tataaaagat cagtatcaga tagagagttt   1080
acactaatga aggcatatga gtatttttaag aaacaatctt ctaaattttt gaacgataca   1140
ctaacgtata tcaaagaaca cccatttaaa gctgtagctg gagtaatgat agcagttttt   1200
accttgatga ccataggcaa ttttttggtct tctttctggt cgaaaccaga gagagatagg   1260
acaacaaaga tgacgggtcg tcagcarggt aatattgttg aattgcccta cagaggkgaa   1320
gaagcgatag attttaagaca tcttgaggaa aaacaattaa tagaytattt gcaccatttt   1380
acatcttcag cgttrgcagg ctcaacatat gcgttcatat ttaaccaacc caatgctgtt   1440
gcctacggta tcttaacagg tgccgtagaa acggcgattg tttatatata cgacaaattt   1500
aggcaacatg gtaaaactgt gacgccagag gttgaagcag caacttcagg tgattgtatg   1560
acgaaagtga aacctcgcgt cattctggag gccacaacat ccggtgatgc acaaacgcag   1620
tatagatcta aaccaaaaat tgaagcattc acgtcggcgg atgtaataac cattactaaa   1680
cccaaagtga tggttgaggc agtgtcatct ggcgatagta taactcaaaa caaacctaaa   1740
gctaagattg aggcaatgac atctggtgac tcacatacca tggtgaaacc taaggctaaa   1800
atagaagcac aaacttcagg agataatatt acaatagtga gacctaaaat actaacagaa   1860
ggagatatta taccagcgaa tatgcaaatg tggaaggatc aagttgcaca aaatttaatt   1920
acccatcgta ttttcaacaa tttatataaa atttcggcta ataattgttc agttcccttg   1980
atgcatggtc ttatggttaa aggacgtatt atgcttattc cagcccacat tttaggatgt   2040
ggtataaaag cagatactga aattaccatg gagaatatgt ttaaagttaa atttacattc   2100
cctttcaaga gcgttaaagt aaacccgcata actaatcgac atggagagtc aaaggaagct   2160
tgtttatttg ggcttccaaa tttggttcat acgcattgtg atattactaa acattttttca   2220
gattcagaag caatgtcatc ttattcacgt gcggaagtta acttaccttt attgcgatat   2280
tcccaacatt tagatagctt tatagtacac attctttcag ctaatgatgc atttgcaatt   2340
```

```
gaccatccca taattcttaa tgatgtagac ttgggcaaac atgttgtgag aagagcattg    2400
gaatatacag caccaacaac aaacggcgat tgtggcgcac cattaatcat caatgaaccc    2460
tctgtcttgc gaaagatagc aggaattcat gttgcaggtg acgcccatgg acgagcttat    2520
tcagaatcaa ttcacaagc tgatttaact cgagcttatc ctgaatttcc agcgcgaatg    2580
caaatttgtc tggactggga taataaaatg aagtttcacc caattgagat taagcaagaa    2640
tacaccaaag ctgactttcc atatgctcca ggagacatgt ttggtcccat aggtaagtgc    2700
ccccaccagt tatttgagcc cggtaaaaca gatattcgac ctagtgtaat ttatggtaag    2760
gtaaaacctc ctattacgaa acccgctatt ttacggcatt ccgaagttaa tatgaaattt    2820
aagaatttgc aaaaatgtgc ttcaaacgta ccgtacatta atgaagattg cttgaggaa    2880
gcatatttag atgtaaagca attatggaat tctaaaagaa atgatgcgtt tcggcggatt    2940
ttaacagatg aagaagtaat taaggaaat gatatttcag aatatatttc tagtataaat    3000
cgacaatcat ccccaggtta cccatggatt ttagatcgta accaggctt tccaggtaag    3060
actcaatggt ttgggaacga tgaagattac aaaattgatc ctgacgtgat gcaaaaagta    3120
catgaaagaa ttgaaaacgc aaaacaagga atacggaccc caacttttg ggttgacacg    3180
ctcaaggatg agcgacgacc tattgagaaa gttgatgcac tcaaaacacg cgtcttttcg    3240
aacggaccca tggattttaa tttggctttc cgcaaatatt ttctaggatt tatagcgcat    3300
ttaatggaaa atcgaataga taatgaagta gcaataggca ccaacgtata tagtagagat    3360
tggacaaaac tggctaagaa attaaaacag aaaggtaaga acgttttgc agggattt    3420
tcaaattttg atggatcctt aaatgccatg attatgtatt tgtttgcccg gatggcaaac    3480
gaattctatg atgatggtaa tgacctgatc cgttatgttt taattgagga gttttgaat    3540
tcagtacatc tttgtgaaca attcttctat atgatgaccc attcccaacc atctggcaat    3600
cctgcaacca ctcccttaaa ttgcttgatc aattcgatag gtttgcggtt gtgtttcctc    3660
cggtgttttg aagaacacaa ggccttcttt atggaactta tgaagaaatt tggctgtaaa    3720
acacggatgg agctattcag attgctagta tcactgatat cctatggaga tgataatgta    3780
atcaatattc accccctgat ttcccattta ttcaatatga atacaatcac aaaatacttt    3840
gcggaatttg gatttacata tacagatgaa acaaagcaag taggaaaagg agtgcctgat    3900
tataaaactc tggaagaagt ttcgtttctc aagagaggt ttatcttcaa tgaggagcga    3960
aattgttatg atgcgccctt ggacatcaat acaattctag agatgattaa ttgggtccgg    4020
aaagatttgg atcaagtgga gagcactaag attaattgtg aaaatgcaat tatgaattg    4080
gctatgcatc cacgggctgt ttttgataag tggaccccac agatcgagaa agcttttat    4140
gacaaaactg gcgtggtctt gaaccacaat tcwtatgacg gctattggca tttacgaaat    4200
atggaatact ttttataaaa cgtttctctt ctggttacca gcaacatagg aaattgtcgt    4260
tgaactacat gttgtaaggc tttagagaaa taagggagtg tcctatttag gatgaggtgc    4320
tccggtggca gccccaccaa aacctctagc gactaggaac agctatatcg ggttgctata    4380
gcagtcagga tgtcattctg gcgttccgaa atacccaaac ctgctcaatc aaacaatgcg    4440
aatactttg agacgaaaac ggcaacaacc tctgcttccc acgcacaatc ggaacttagc    4500
gagacgaccc cagaaaattc ccttaccaga caagaactca cagttttcca tgatgttgaa    4560
caacctcgcg tcgctcttcc aattgctccg caaacgacta gctctcttgc taagcttgat    4620
tctacagcga caattgtgga ttttcttttct agaactgttg tcctcgatca attcgagctt    4680
gttcaaggtg aatcaaacga taaccacaaa ccccttaacg cagcaacttt taaagacccc    4740
```

```
caaccagcca tcagacagta ttccttgcca ggagacattc ttaagctggg tggcaagtta    4800
gataaggcaa ataaccatca atactttaag gcagattgtc acataaaatt agttttaaat    4860
acaaatccca tggtggccgg aagattttgg ctaacatatt ccccatatga acataaagta    4920
gataaggcaa gacgccagca atataatagt agagctggag tgacagcata tcctggaata    4980
gaaatggatg ttcaaatcaa tgattcagca gaaatggtta tcccatttgc ttcctacaaa    5040
gaagcttatg atttaaatac tcccacccct gaagattttg ttacattatc tttattcggt    5100
ataacagatt tactagctaa aaatggtaat aattacgcag taggaattac catcttagcc    5160
tggtttgaaa acataacaat taatctacct acaataaaga atatcccata caggcaatta    5220
ccccacacca atactaatac taagaaaatt gaaatagatc gcaaattagc taaattagaa    5280
aagaagaatc cttcggccta taaatatata actaatattt tagatatacg accagccacc    5340
atgcaaaccg catggggtgc cccatcacag ttgctaatta aagatattct agatctagca    5400
ccagtgctta atgaacttca agcagtattg tctgatgtgt gtggatcaat taggaaccga    5460
gacttttcgt tgaggccctt gtataaagta cgcatacatg caatgcaaga cttaatcaat    5520
gattccctaa agaggatgtt tgatacatat gaggccctgg acgagacgga tcttatgagt    5580
gaagacacac cagataatgc ttttccaact atggttttat acttagattc ccttaagaaa    5640
attaacaagt caaaatcaga gtatgttgag atgcagttgg atgcctatga tgcacgggat    5700
attgatggta tgctgaatgc gtacgatcaa ttgaaagagt ttaaccatca tacagcaaga    5760
aaggaaatgg tgtcaatgat gcatctgggc taccaatatt ctcaacgacg acaccgacgt    5820
gatgtgacag cagcgagagc catagcggat atgatacttg tcgacgagcg tgatgcgacg    5880
atgcaagtgc aagcagaagt aggaggacag ggtttgatca ctgacatagc ttccaccgtt    5940
tcggcggtgg caggtgcggt cagtggtatc cctgtcatac gtgaaatagc atctaccgtt    6000
ggttgggttt ctgacatagt tggaggaatt cctctatatct ttggatggtc tcgaccaaat    6060
gatatggaga aagtgacatc tttggctaac gtccccggca agtattattc ccatgtaaaa    6120
gcgatagata atagtgtagc tttagctttg agtaatgaga acgagcttct cccacttagc    6180
gacatctttc cctcagcggt agatgagatg gacttggcat atgtgtgtgc taatcctgga    6240
gtgaaggaag tcattacgcg gtcgaaaacg dacccyatga atagaacttt agctttaatg    6300
gaagtgggat tacctagttt taatagatac caagataagg caatagattg tgatagtgaa    6360
cctaccccat ataatatctg taacaaagrt ttgatcaaac caaatgggaa catcattttg    6420
agccctggag atctggtgca gatgaagggc agcttggctg cgacaatttt ggatactgtt    6480
ccttgtgaat atgtgtccca attgtttcag tattggcgtg ctaccatttg ctttaagatt    6540
tctgtggtaa agaccggttt tcatacagga cgtttagaaa ttttctttga cccgggtgag    6600
tatctaacga atcctaaggc ggattggcat aattatgttg atctttccgc ttacgataaa    6660
gtggataccg caaattctta caaatatatt ttagatttaa caaatgattc agaaattact    6720
attagagtgc catttattag cgataggtta gctttaagta caattggtgc taatagttat    6780
ggtgaggacg gtgtaatggg accccccaaat ttgaatgata ttttcgattc aatgattggg    6840
tctctaatca tcagaccgct tacaaaactt atggcgccag atacagtttc agatcaagtt    6900
aaaatagtaa tttggaaatg gcagaggat gtacagctcc ttgttcccaa agaatcgaac    6960
cagctcgaaa tagttccata cgagttcgag cgaacaccag gtttgacctg caagaaacag    7020
aaaatatcag atgaagatat gaaggtgttt attgcacatt gggaaaaaga tggcaaatgg    7080
atttgtactt cagacccaac tacaagcatg gttttctcat ggggacaata tcccttatgt    7140
```

-continued

```
gagactagaa atgccacaat gcagatcaac atttccaatg aagcatcagg aaacagtatc    7200
gatattttcc aggataataa tgcaggtgtg agtccaaatg cagtaatggg taaaattgcg    7260
ggtgaacgtc tagttaactt gcgaccacta ctgcgctgct tccgatcttt gggtggcata    7320
acgcttgatc gggcaggaca aattctgtct gaaagagtgt attggaacca caagattat    7380 gttagcatac tctcatatct gtatcgtttt tccagagggg gatatcgtta caaattcttt    7440
gcagacgata acgaacaggg acaagtcatg tcaacgcttg tcaaaaatta ctacaaggac    7500
catgcaacaa gtactggtcc atcccatatg acttacaata atattaatcc cgtacatgaa    7560
attatgatcc catattattc tcaatatagg aaaatcccaa tttcaggcga agtagaatta    7620
attaaaggta agattcaaac tcccgtagaa aagggcatta aggtgagct ttatcgctca    7680 ggaaatgatg acctaaccta tgggtggatc gttggatcgc cccagcttta tgttggagcg    7740
gctcaacgat ggagttgttg gacagtaaca aagccaacac aactagtcac taaggaaact    7800
taatggatag taaattttgc tcttcaaaga cagtcaaatc tttggagttc ggttttattc    7860
ttcaaaattc ttttaaaaca gaggatgcat agttaatggc gagcactatc gtccggaatg    7920
acaccgttga gaaaactcac tagatggagg ctcattggtt atcagcgttc tgggataatc    7980
taacgattag ttatgcaaac gcatattcaa gtaaattaca attaag                  8026
```

```
<210> SEQ ID NO 2
<211> LENGTH: 25
<212> TYPE: DNA
<213> ORGANISM: Solenopsis Invicta Virus

<400> SEQUENCE: 2
ggaagtcatt acgtggtcga aaacg                                          25

<210> SEQ ID NO 3
<211> LENGTH: 39
<212> TYPE: DNA
<213> ORGANISM: Solenopsis Invicta Virus

<400> SEQUENCE: 3
cgtcctgtat gaaaaccggt ctttaccaca gaaatctta                           39

<210> SEQ ID NO 4
<211> LENGTH: 24
<212> TYPE: DNA
<213> ORGANISM: Solenopsis Invicta Virus

<400> SEQUENCE: 4
ggaagtcatt acgtggtcga aaac                                           24

<210> SEQ ID NO 5
<211> LENGTH: 28
<212> TYPE: DNA
<213> ORGANISM: Solenopsis Invicta Virus

<400> SEQUENCE: 5
ccaagctgcc cttcatctgc accagatc                                       28

<210> SEQ ID NO 6
<211> LENGTH: 27
<212> TYPE: DNA
<213> ORGANISM: Solenopsis Invicta Virus

<400> SEQUENCE: 6
ttcatctgca ccagatctcc agggctc                                        27
```

```
<210> SEQ ID NO 7
<211> LENGTH: 26
<212> TYPE: DNA
<213> ORGANISM: Solenopsis Invicta Virus

<400> SEQUENCE: 7
caatgattca gcagaaatgg ttatcc                                          26

<210> SEQ ID NO 8
<211> LENGTH: 21
<212> TYPE: DNA
<213> ORGANISM: Solenopsis Invicta Virus

<400> SEQUENCE: 8
gtcacatcac gtcggtgtcg t                                               21

<210> SEQ ID NO 9
<211> LENGTH: 20
<212> TYPE: DNA
<213> ORGANISM: Solenopsis Invicta Virus

<400> SEQUENCE: 9
tctgccttaa agtattgatg                                                 20

<210> SEQ ID NO 10
<211> LENGTH: 33
<212> TYPE: DNA
<213> ORGANISM: Solenopsis Invicta Virus

<400> SEQUENCE: 10
gtctcctggc aaggaatact gtctgatggc tgg                                  33

<210> SEQ ID NO 11
<211> LENGTH: 29
<212> TYPE: DNA
<213> ORGANISM: Solenopsis Invicta Virus

<400> SEQUENCE: 11
ggaagagcga cgcgaggttg ttcaacatc                                       29

<210> SEQ ID NO 12
<211> LENGTH: 31
<212> TYPE: DNA
<213> ORGANISM: Solenopsis Invicta Virus

<400> SEQUENCE: 12
cgcatcaact ttctcaatgg gtcgtcgctc a                                    31

<210> SEQ ID NO 13
<211> LENGTH: 23
<212> TYPE: DNA
<213> ORGANISM: Solenopsis Invicta Virus

<400> SEQUENCE: 13
cagtgatact agcaatctga ata                                             23

<210> SEQ ID NO 14
<211> LENGTH: 22
<212> TYPE: DNA
<213> ORGANISM: Solenopsis Invicta Virus

<400> SEQUENCE: 14
ctatctaaat gttgggaata tc                                              22
```

```
<210> SEQ ID NO 15
<211> LENGTH: 28
<212> TYPE: DNA
<213> ORGANISM: Solenopsis Invicta Virus

<400> SEQUENCE: 15
caccggatgt tgtggcctcc agaatgac                                              28

<210> SEQ ID NO 16
<211> LENGTH: 33
<212> TYPE: DNA
<213> ORGANISM: Solenopsis Invicta Virus

<400> SEQUENCE: 16
aatggaagaa gacacttcga tgtggcacga ctc                                        33

<210> SEQ ID NO 17
<211> LENGTH: 34
<212> TYPE: DNA
<213> ORGANISM: Solenopsis Invicta Virus

<400> SEQUENCE: 17
gaatcgtgcc acatcgaagt gtcttcttcc attg                                       34

<210> SEQ ID NO 18
<211> LENGTH: 20
<212> TYPE: DNA
<213> ORGANISM: Solenopsis Invicta Virus

<400> SEQUENCE: 18
cattgggttg gttaaatatg                                                       20

<210> SEQ ID NO 19
<211> LENGTH: 25
<212> TYPE: DNA
<213> ORGANISM: Solenopsis Invicta Virus

<400> SEQUENCE: 19
cacaactggt tgggttcgag gtttg                                                 25

<210> SEQ ID NO 20
<211> LENGTH: 21
<212> TYPE: DNA
<213> ORGANISM: Solenopsis Invicta Virus

<400> SEQUENCE: 20
tgacttacct acgccacttt c                                                     21

<210> SEQ ID NO 21
<211> LENGTH: 2864
<212> TYPE: DNA
<213> ORGANISM: Solenopsis Invicta Virus
<300> PUBLICATION INFORMATION:
<301> AUTHORS: Steven Valles and Charles A. Strong
<302> TITLE: Solenopsis invicta virus-1A (SINV-1A): Distinct species or
      genotype of SINV-1
<303> JOURNAL: Journal of Invertebrate Pathology
<304> VOLUME: 88
<306> PAGES: 232-237
<307> DATE: 2005-03-25
<300> PUBLICATION INFORMATION:
<308> DATABASE ACCESSION NUMBER: GenBank
<309> DATABASE ENTRY DATE: 2005-07-25
<313> RELEVANT RESIDUES IN SEQ ID NO: (1)..(2864)
```

```
<400> SEQUENCE: 21
taatctacct acaataaaga atatcccata tagacaatta ccccaaacta ataccaatgc    60
aaagaagatt gaaatagatc gaaaattggc taaattagaa aagaagaacc cttccgctta   120
taaatatata actaatattt tagatatacg gccggccacc atgcagaccg catggggcac   180
tccatcacaa ttattaatta aggatgtttt agatttagca ccggtattta acgaacttca   240
agcagtatta tctgaagtgt gtggatcaat taggaaccga acttttcgt tgaggccttt    300 atataaagta cgcatacatg ctatgcaaga cttaatcaat gattccttaa agaggatgtt   360
tgatagatat gaggccctgg acgagacgga tcttatgagt gaagacacac cagataatgc   420
tttcccaact atggttttat atttggattc ccttaagaaa attaataagt caaaatcaga   480
gtatgtggag atgcaattgg atgcctatga tgcacgagat attgatggta tgttaaatgc   540
atataatcaa ttgaaagagt taatcacca tacagcaaga aaggagatgg tgtcaatgat    600
gcatctgggt tatcaatatt cccaacggcg gcaccgacga gatgtaacag cagcaagagc   660
catagcagat acaatacttg tagatgaacg cgatgcaaca atgcaagtcc aagcagaagt   720
aggaggacag ggtcttatta ctgacatagc ctctaccgtt tcggcggtgg cgggtgcagt   780
cagtggtatc ccggttatag gagaaattgc atctacagtt ggttgggttt ctgatatagt   840
tggaggaatt tcctccatct ttggatggtc tcgaccaaat gacatggaaa agtaacatc    900 tttggcaaac gttcctggca agtattattc tcacgtaaaa gcagtagata atagtgtagc   960
tttagctttg agtaatgaga acgaacttct cccgcttagt gacatctttc cctcagcagt  1020
agatgagatg gatttggcat acgtgtgtgc caaccccgga gtgaaggagg tcattacatg  1080
gtcgaagaca gatcccatga ataagacttt agcattaatg gaagtaggat tacctagttt  1140
taatagatat caggataagg caatagattg tgatagtgaa cccactccat acaacatttg  1200
taataaagat ttaattaaac caaatgggaa tattattttg agccctgggg atctggtgca  1260
gatgaaaggt agcctggctg cgacaatctt ggacactgtt ccatgcgaat acgtgtctca  1320 gttgttcag tattggcgtg ctacaatttg ctttaagatt tccgtggtga aaactggttt   1380
ccatacagga cgtttggaga ttttctttga ccctggtgag tatcttacta atcctaaggc  1440
ggattggcat aattatgttg atcttcggc ttatgataag gtggatactg caaattctta   1500
caaatatatt ttagatttaa cgaatgattc agaaattacc attagagtac catttattag  1560
tgataggtta gctttaagca caatcggtgc aatagttat ggtgaggatg gtgtgatggg   1620
acccccaaat ttgaacgata ttttcgattc aatgattggg tctctgatca tcaggccgct  1680
cacgaggctt atggcgccag atacagtttc agatcaggtt aaaatagtaa tttggaaatg  1740
ggctgaagat gtgcagctcc ttgttcctaa agaatcaaat caactcgaaa tcgttccata  1800
cgagtttgag cgaacaccag gtttgacatg caagaaacaa aagatttctg atcaagatat  1860
gaaggtgttt attgcgcatt gggaaaaaga tggtcaatgg gtttgtactt cagacccaac  1920
cacaagcatg gtcttttcat ggggacaata tcccttatgt gagaccagaa atgctacgat  1980
gcagataaac atttctaatg aagcttcagg aaatagtatt gatattttcc aggataataa  2040
tgcaggtgta agtccaaacg cagttatggg gaaaattgca ggtgaacgtt tagttaacct  2100
acgaccatta ttgcgatgct ttcgttcctt gggtggcata acgctggatc gggcaggtca  2160
aatcctgtct gagagagtgt attggcatta taaggattac gttagcatac tttcatacct  2220
gtatcgattt tctagaggag gatatcgcta caagtttttt gcagatgaca acgaacaagg  2280
acaagtcatg tcaacgcttg ttaaaaatta ccacaaggac catgctacaa gcactggtcc  2340
```

-continued

```
ttcccatatg acttacaata atctcaaccc cgtacacgaa attatgatcc catattattc    2400
tcaatatagg aaaattccaa tttcaggcga agtagaatta attaaaggta agattcagac    2460
acctgtagaa aagggcatta aaggtgagct ttatcgctca ggaaatgatg acctgacata    2520
cgggtggatc gttggatcgc cccaacttta tgttggagca gctcaacggt ggagttgttg    2580
gacagtaaca aagccaacac aactaggcac taaggaaact taatggatag taaattttgc    2640
tcttcaggga cagtcaaatc tctggagttc ggttttattc ttcaaaattc ttttaaaaca    2700
gaggacgtat gtggaatggc gagcactatt gttcggattg acgattttga gaaaactcac    2760
tagatggagg ctcttgatct attagcagtc tgagataatc taacgatttc acatgcgaac    2820
gcatattcaa gtaaattaaa ttaagaaaaa aaaaaaaaa aaaa                       2864
```

```
<210> SEQ ID NO 22
<211> LENGTH: 30
<212> TYPE: DNA
<213> ORGANISM: Solenopsis Invicta Virus

<400> SEQUENCE: 22
gcgataggtt agctttaagt acaattggtg                                        30

<210> SEQ ID NO 23
<211> LENGTH: 25
<212> TYPE: DNA
<213> ORGANISM: Solenopsis Invicta Virus

<400> SEQUENCE: 23
tcccaatgtg caataaacac cttca                                             25

<210> SEQ ID NO 24
<211> LENGTH: 29
<212> TYPE: DNA
<213> ORGANISM: Solenopsis Invicta Virus

<400> SEQUENCE: 24
cgccttagga ttcgttagat actcacccg                                         29

<210> SEQ ID NO 25
<211> LENGTH: 22
<212> TYPE: DNA
<213> ORGANISM: Solenopsis Invicta Virus

<400> SEQUENCE: 25
cttgatcggg caggacaaat tc                                                22

<210> SEQ ID NO 26
<211> LENGTH: 22
<212> TYPE: DNA
<213> ORGANISM: Solenopsis Invicta Virus

<400> SEQUENCE: 26
gaacgctgat aaccaatgag cc                                                22

<210> SEQ ID NO 27
<211> LENGTH: 34
<212> TYPE: DNA
<213> ORGANISM: Solenopsis Invicta Virus

<400> SEQUENCE: 27
cactccatac aacatttgta ataaagattt aatt                                   34
```

```
<210> SEQ ID NO 28
<211> LENGTH: 25
<212> TYPE: DNA
<213> ORGANISM: Solenopsis Invicta Virus

<400> SEQUENCE: 28
ccaatactga aacaactgag acacg                                            25

<210> SEQ ID NO 29
<211> LENGTH: 25
<212> TYPE: DNA
<213> ORGANISM: Solenopsis Invicta Virus

<400> SEQUENCE: 29
ccaatactga aacaactgag acacg                                            25

<210> SEQ ID NO 30
<211> LENGTH: 32
<212> TYPE: DNA
<213> ORGANISM: Solenopsis Invicta Virus

<400> SEQUENCE: 30
cttaattgta atttacttga atatgcgttt gc                                    32

<210> SEQ ID NO 31
<211> LENGTH: 27
<212> TYPE: DNA
<213> ORGANISM: Solenopsis Invicta Virus

<400> SEQUENCE: 31
gtatctaacg aatcctaagg cggattg                                          27

<210> SEQ ID NO 32
<211> LENGTH: 27
<212> TYPE: DNA
<213> ORGANISM: Solenopsis Invicta Virus

<400> SEQUENCE: 32
caatccgcct taggattcgt tagatac                                          27

<210> SEQ ID NO 33
<211> LENGTH: 27
<212> TYPE: DNA
<213> ORGANISM: Solenopsis Invicta Virus

<400> SEQUENCE: 33
cggatcttat gagtgaagac acaccag                                          27

<210> SEQ ID NO 34
<211> LENGTH: 21
<212> TYPE: DNA
<213> ORGANISM: Solenopsis Invicta Virus

<400> SEQUENCE: 34
caacctctgc ttcccacgca c                                                21

<210> SEQ ID NO 35
<211> LENGTH: 26
<212> TYPE: DNA
<213> ORGANISM: Solenopsis Invicta Virus

<400> SEQUENCE: 35
gatggtctcg accaaatgat atggag                                           26
```

```
<210> SEQ ID NO 36
<211> LENGTH: 31
<212> TYPE: DNA
<213> ORGANISM: Solenopsis Invicta Virus

<400> SEQUENCE: 36
atgaagatat gaaggtgttt attgcacatt g                                      31

<210> SEQ ID NO 37
<211> LENGTH: 24
<212> TYPE: DNA
<213> ORGANISM: Solenopsis Invicta Virus

<400> SEQUENCE: 37
cacataaggg atattgtccc catg                                              24

<210> SEQ ID NO 38
<211> LENGTH: 24
<212> TYPE: DNA
<213> ORGANISM: Solenopsis Invicta Virus

<400> SEQUENCE: 38
tggacgagac ggatcttatg agtg                                              24

<210> SEQ ID NO 39
<211> LENGTH: 25
<212> TYPE: DNA
<213> ORGANISM: Solenopsis Invicta Virus

<400> SEQUENCE: 39
gctgtcaacg atacgctacg taacg                                             25

<210> SEQ ID NO 40
<211> LENGTH: 53
<212> TYPE: PRT
<213> ORGANISM: Solenopsis Invicta Virus

<400> SEQUENCE: 40

Pro Arg Thr Gln Pro Val Val Ile Trp Leu Phe Gly Glu Ser Gly Val
1               5                   10                  15

Gly Lys Ser Gly Gln Asn Val Val Thr Tyr Asp Asp Phe Gly Glu Met
            20                  25                  30

Ala His Leu Glu Asp Lys Arg Lys Thr Lys Phe Thr Ser Lys Ile Leu
        35                  40                  45

Leu Met Thr Ser Asn
    50

<210> SEQ ID NO 41
<211> LENGTH: 53
<212> TYPE: PRT
<213> ORGANISM: Solenopsis Invicta Virus
<220> FEATURE:
<221> NAME/KEY: misc_feature
<222> LOCATION: (26)..(26)
<223> OTHER INFORMATION: Xaa can be any naturally occurring amino acid

<400> SEQUENCE: 41

Pro Arg Thr Gln Pro Ile Val Ile Trp Leu Phe Gly Glu Ser Gly Arg
1               5                   10                  15

Gly Lys Ser Gly Gln Asn Ile Val Cys Xaa Asp Asp Phe Gly Glu Met
            20                  25                  30
```

```
Ala His Leu Glu Asp Lys Arg Lys Thr Lys Phe Thr Ser Lys Val Ile
        35                  40                  45

Ile Met Thr Ser Asn
    50

<210> SEQ ID NO 42
<211> LENGTH: 52
<212> TYPE: PRT
<213> ORGANISM: Solenopsis Invicta Virus

<400> SEQUENCE: 42

Val Arg Tyr Lys Pro Phe Val Ile Cys Ile Glu Gly Pro Ala Gly Ile
1               5                   10                  15

Gly Lys Ser Lys Gln Pro Val Val Tyr Asp Asp Trp Ala Lys Met
            20                  25                  30

Ala His Leu Glu Glu Lys Lys Ile Arg Gly Asn Pro Leu Ile Val Ile
        35                  40                  45

Leu Leu Cys Asn
    50

<210> SEQ ID NO 43
<211> LENGTH: 53
<212> TYPE: PRT
<213> ORGANISM: Solenopsis Invicta Virus

<400> SEQUENCE: 43

Val Arg Asn Pro Pro Val Thr Leu Tyr Leu Tyr Gly Glu Thr Gly Val
1               5                   10                  15

Gly Lys Ser Thr Gln Leu Val Thr Val Phe Asp Asp Phe Asn His Met
            20                  25                  30

Ala Ser Ile Glu Glu Lys Ala Asn Thr Val Phe Gln Ser Lys Val Ile
        35                  40                  45

Leu Cys Ser Ser Asn
    50

<210> SEQ ID NO 44
<211> LENGTH: 52
<212> TYPE: PRT
<213> ORGANISM: Solenopsis Invicta Virus

<400> SEQUENCE: 44

Val Arg Lys Met Pro Phe Thr Ile Phe Phe Gln Gly Lys Ser Arg Thr
1               5                   10                  15

Gly Lys Ser Leu Gln Pro Pro Val Leu Met Asp Asp Phe Ala Asn Met
            20                  25                  30

Ala Gly Leu Glu Glu Lys Gly Ile Cys Phe Asp Ser Gln Phe Val Phe
        35                  40                  45

Val Ser Thr Asn
    50

<210> SEQ ID NO 45
<211> LENGTH: 52
<212> TYPE: PRT
<213> ORGANISM: Solenopsis Invicta Virus

<400> SEQUENCE: 45

Thr Arg Cys Glu Pro Val Val Cys Tyr Leu Tyr Gly Lys Arg Gly Gly
1               5                   10                  15

Gly Lys Ser Leu Gln Leu Val Cys Ile Ile Asp Asp Ile Gly Asn Met
            20                  25                  30
```

-continued

Ala Ser Leu Glu Glu Lys Gly Arg His Phe Ser Ser Pro Phe Ile Ile
             35                  40                  45

Ala Thr Ser Asn
        50

<210> SEQ ID NO 46
<211> LENGTH: 44
<212> TYPE: PRT
<213> ORGANISM: Solenopsis Invicta Virus

<400> SEQUENCE: 46

Leu Ile Pro Ala His Ile Leu Gly Cys Gly Glu Ser Lys Glu Ala Ala
1               5                   10                  15

Pro Thr Thr Asn Gly Asp Cys Gly Ala Pro Leu Ile Ile Asn Glu Pro
                20                  25                  30

Ser Val Leu Arg Lys Ile Ala Gly Ile His Val Ala
            35                  40

<210> SEQ ID NO 47
<211> LENGTH: 45
<212> TYPE: PRT
<213> ORGANISM: Solenopsis Invicta Virus

<400> SEQUENCE: 47

Met Leu Ala Pro Gly His Leu Val Gly Phe Gly Glu Ser Lys Glu Ala
1               5                   10                  15

Met Pro Thr Thr Asn Gly Asp Cys Gly Ala Pro Leu Val Ile Asn Glu
                20                  25                  30

Thr Gln Val Ile Arg Lys Ile Ala Gly Ile His Val Ala
            35                  40                  45

<210> SEQ ID NO 48
<211> LENGTH: 42
<212> TYPE: PRT
<213> ORGANISM: Solenopsis Invicta Virus

<400> SEQUENCE: 48

Ala Leu Leu Pro Arg His Tyr Val Arg Ala Ser Glu Ser Thr Asp Leu
1               5                   10                  15

Tyr Ser Gln Gln Gly Ala Cys Gly Ser Leu Cys Phe Leu Ser Arg Ser
                20                  25                  30

Gln Arg Pro Ile Val Gly Met His Phe Ala
            35                  40

<210> SEQ ID NO 49
<211> LENGTH: 46
<212> TYPE: PRT
<213> ORGANISM: Solenopsis Invicta Virus

<400> SEQUENCE: 49

Ala Val Ala Pro Gly His Tyr Leu Arg Ile Leu Asp Ser Arg Asp Leu
1               5                   10                  15

Leu Glu Thr Ile Ser Gly Asp Cys Gly Ala Pro Leu Phe Val Thr Asn
                20                  25                  30

Ser Lys Ile Gly Pro Gly Lys Ile Ile Gly Ile His Thr Ala
            35                  40                  45

<210> SEQ ID NO 50
<211> LENGTH: 43
<212> TYPE: PRT
<213> ORGANISM: Solenopsis Invicta Virus -continued

```
<400> SEQUENCE: 50

Phe Leu Ala Cys Lys His Phe Thr His Ile Pro Asp Ser Glu Leu
1               5                   10                  15

Ala Pro Thr Ile Pro Glu Asp Cys Gly Ser Leu Val Ile Ala His Ile
            20                  25                  30

Gly Gly Lys His Lys Ile Val Gly Val His Val
            35                  40

<210> SEQ ID NO 51
<211> LENGTH: 45
<212> TYPE: PRT
<213> ORGANISM: Solenopsis Invicta Virus

<400> SEQUENCE: 51

Leu Leu Val Pro Ser His Ala Tyr Lys Phe Val Gly Phe Gln Asp Val
1               5                   10                  15

Gly Glu Gly Leu Pro Gly Met Cys Gly Gly Ala Leu Val Ser Ser Asn
            20                  25                  30

Gln Ser Ile Gln Asn Ala Ile Leu Gly Ile His Val Ala
            35                  40                  45

<210> SEQ ID NO 52
<211> LENGTH: 74
<212> TYPE: PRT
<213> ORGANISM: Solenopsis Invicta Virus

<400> SEQUENCE: 52

Leu Lys Asp Glu Arg Arg Pro Ile Glu Lys Val Asp Ala Leu Lys Thr
1               5                   10                  15

Arg Val Phe Ser Asn Gly Pro Met Asp Phe Asn Leu Ala Phe Arg Lys
            20                  25                  30

Tyr Phe Leu Gly Phe Ile Ala His Leu Met Glu Asn Arg Ile Asp Asn
            35                  40                  45

Glu Val Ala Ile Gly Thr Asn Val Tyr Ser Arg Asp Trp Thr Gly Asp
    50                  55                  60

Phe Ser Asn Phe Asp Gly Ser Leu Asn Ala
65                  70

<210> SEQ ID NO 53
<211> LENGTH: 74
<212> TYPE: PRT
<213> ORGANISM: Solenopsis Invicta Virus

<400> SEQUENCE: 53

Leu Lys Asp Glu Arg Arg Pro Ile Glu Lys Val Asp Gln Leu Lys Thr
1               5                   10                  15

Arg Val Phe Ser Asn Gly Pro Met Asp Phe Ser Ile Thr Phe Arg Met
            20                  25                  30

Tyr Tyr Leu Gly Phe Ile Ala His Leu Met Glu Asn Arg Ile Thr Asn
            35                  40                  45

Glu Val Ser Ile Gly Thr Asn Val Tyr Ser Gln Asp Trp Asn Gly Asp
    50                  55                  60

Phe Ser Thr Phe Asp Gly Ser Leu Asn Val
65                  70

<210> SEQ ID NO 54
<211> LENGTH: 75
<212> TYPE: PRT
<213> ORGANISM: Solenopsis Invicta Virus
```

<400> SEQUENCE: 54

Leu Lys Asp Glu Arg Lys Leu Pro Glu Lys Val Arg Lys Tyr Gly Gly
1               5                   10                  15

Thr Arg Val Phe Cys Asn Pro Pro Ile Asp Tyr Ile Val Ser Met Arg
            20                  25                  30

Gln Tyr Tyr Met His Phe Val Ala Ala Phe His Glu Gln Arg Phe Lys
        35                  40                  45

Leu Met His Ala Val Gly Ile Asn Val Gln Ser Thr Glu Trp Thr Ile
    50                  55                  60

Asp Tyr Ser Asn Phe Gly Pro Gly Phe Asn Ala
65                  70                  75

<210> SEQ ID NO 55
<211> LENGTH: 72
<212> TYPE: PRT
<213> ORGANISM: Solenopsis invicta

<400> SEQUENCE: 55

Leu Lys Asp Glu Arg Lys Pro Lys Glu Lys Ala His Lys Ser Arg Met
1               5                   10                  15

Phe Ser Asn Gly Pro Ile Asp Tyr Leu Val Trp Ser Lys Met Tyr Phe
            20                  25                  30

Asn Pro Ile Val Ala Val Leu Ser Glu Leu Lys Asn Val Asp His Ile
        35                  40                  45

Ser Val Gly Ser Asn Val Tyr Ser Thr Asp Trp Asp Gly Asp Phe Glu
    50                  55                  60

Gly Phe Asp Ala Ser Glu Gln Ser
65                  70

<210> SEQ ID NO 56
<211> LENGTH: 74
<212> TYPE: PRT
<213> ORGANISM: Solenopsis Invicta Virus

<400> SEQUENCE: 56

Lys Asp Glu Lys Leu Pro Met Arg Lys Val Phe Asp Lys Pro Lys Thr
1               5                   10                  15

Arg Cys Phe Thr Ile Leu Pro Met Glu Tyr Asn Leu Val Val Arg Arg
            20                  25                  30

Lys Phe Leu Asn Phe Val Arg Phe Ile Met Ala Asn Arg His Arg Leu
        35                  40                  45

Ser Cys Gln Val Gly Ile Asn Pro Tyr Ser Met Glu Trp Ser Cys Asp
    50                  55                  60

Tyr Ser Ser Phe Asp Gly Leu Leu Ser Lys
65                  70

<210> SEQ ID NO 57
<211> LENGTH: 74
<212> TYPE: PRT
<213> ORGANISM: Solenopsis Invicta Virus

<400> SEQUENCE: 57

Pro Lys Asp Glu Leu Arg Pro Leu Glu Lys Val Leu Glu Ser Lys Thr
1               5                   10                  15

Arg Ala Ile Asp Ala Cys Pro Leu Asp Tyr Ser Ile Leu Cys Arg Met
            20                  25                  30

Tyr Trp Gly Pro Ala Ile Ser Tyr Phe His Leu Asn Pro Gly Phe His
        35                  40                  45

```
Thr Gly Val Ala Ile Gly Ile Asp Pro Asp Arg Gln Trp Asp Leu Asp
         50                  55                  60

Phe Ser Ala Phe Asp Ala Ser Leu Ser Pro
 65                  70

<210> SEQ ID NO 58
<211> LENGTH: 67
<212> TYPE: PRT
<213> ORGANISM: Solenopsis Invicta Virus

<400> SEQUENCE: 58

Thr His Ser Gln Pro Ser Gly Asn Pro Ala Thr Thr Pro Leu Asn Cys
 1               5                  10                  15

Leu Ile Asn Ser Ile Gly Leu Leu Ile Ser Tyr Gly Asp Asp Asn Val
             20                  25                  30

Ile Thr Leu Glu Glu Val Ser Phe Leu Lys Arg Gly Phe Ile Phe Asn
         35                  40                  45

Glu Glu Arg Asn Cys Tyr Asp Ala Pro Leu Asp Ile Asn Thr Ile Leu
     50                  55                  60

Glu Met Ile
 65

<210> SEQ ID NO 59
<211> LENGTH: 67
<212> TYPE: PRT
<213> ORGANISM: Solenopsis Invicta Virus

<400> SEQUENCE: 59

Thr His Ser Gln Pro Ser Gly Asn Pro Ala Thr Thr Pro Leu Asn Cys
 1               5                  10                  15

Phe Ile Asn Ser Met Gly Leu Ile Val Ser Tyr Gly Asp Asp Asn Val
             20                  25                  30

Ile Thr Ile Glu Asp Val Gln Tyr Leu Lys Arg Lys Phe Arg Tyr Asp
         35                  40                  45

Ser Lys Arg Lys Val Trp Glu Ala Pro Leu Cys Met Asp Thr Ile Leu
     50                  55                  60

Glu Met Pro
 65

<210> SEQ ID NO 60
<211> LENGTH: 68
<212> TYPE: PRT
<213> ORGANISM: Solenopsis Invicta Virus

<400> SEQUENCE: 60

Lys Cys Gly Ser Pro Ser Gly Ala Pro Ile Thr Val Val Ile Asn Thr
 1               5                  10                  15

Leu Val Asn Ile Leu Tyr Ile Leu Phe Cys Tyr Gly Asp Asp Leu Ile
             20                  25                  30

Met Thr Leu Leu Asn Ser Thr Phe Leu Lys His Gly Phe His Pro His
         35                  40                  45

Glu Val Tyr Pro His Leu Trp Gln Ser Ala Leu Ala Trp Ser Ser Ile
     50                  55                  60

Asn Asp Thr Thr
 65

<210> SEQ ID NO 61
<211> LENGTH: 68
<212> TYPE: PRT
<213> ORGANISM: Solenopsis Invicta Virus
```

```
<400> SEQUENCE: 61

Trp Cys Lys Ser Leu Pro Ser Gly His Tyr Leu Thr Ala Ile Ile Asn
1               5                   10                  15

Ser Val Phe Val Asn Leu Val Met Ile Val Ala Tyr Gly Asp Asp His
            20                  25                  30

Val Val Arg Leu Glu Asp Val Ser Tyr Leu Lys Arg Asn Phe Val Tyr
        35                  40                  45

Asp Glu Ser Arg Gln Arg Tyr Ile Ala Pro Leu Ser Leu Asp Val Val
    50                  55                  60

Leu Glu Met Pro
65

<210> SEQ ID NO 62
<211> LENGTH: 66
<212> TYPE: PRT
<213> ORGANISM: Solenopsis Invicta Virus

<400> SEQUENCE: 62

Glu Cys Gly Ile Pro Ser Gly Phe Pro Met Thr Val Ile Val Asn Ser
1               5                   10                  15

Ile Phe Asn Glu Ile Leu Ile Leu Val Thr Tyr Gly Asp Asp Asn Leu
            20                  25                  30

Ile Arg Leu Glu Glu Cys Asp Phe Leu Lys Arg Thr Phe Val Gln Arg
        35                  40                  45

Ser Ser Thr Ile Trp Asp Ala Pro Glu Asp Lys Ala Ser Leu Trp Ser
    50                  55                  60

Gln Leu
65

<210> SEQ ID NO 63
<211> LENGTH: 65
<212> TYPE: PRT
<213> ORGANISM: Solenopsis Invicta Virus

<400> SEQUENCE: 63

Cys Gly Ser Met Pro Ser Gly Ser Pro Cys Thr Ala Leu Leu Asn Ser
1               5                   10                  15

Ile Ile Asn Asn Val Asn Leu Cys Tyr Gly Asp Asp Val Leu Ile Pro
            20                  25                  30

Val Ser Glu Leu Thr Phe Leu Lys Arg Ser Phe Asn Leu Val Glu Asp
        35                  40                  45

Arg Ile Arg Pro Ala Ile Ser Glu Lys Thr Ile Trp Ser Leu Ile Ala
    50                  55                  60

Trp
65

<210> SEQ ID NO 64
<211> LENGTH: 56
<212> TYPE: PRT
<213> ORGANISM: Solenopsis Invicta Virus

<400> SEQUENCE: 64

Gln Leu Phe Gln Tyr Trp Arg Ala Thr Ile Cys Phe Lys Ile Ser Val
1               5                   10                  15

Val Lys Thr Gly Phe His Thr Gly Arg Leu Glu Ile Phe Phe Asp Pro
            20                  25                  30
```

```
Gly Tyr Lys Tyr Ile Leu Asp Leu Thr Asn Asp Ser Glu Ile Thr Ile
            35                  40                  45

Arg Val Pro Phe Ile Ser Asp Arg
        50                  55

<210> SEQ ID NO 65
<211> LENGTH: 56
<212> TYPE: PRT
<213> ORGANISM: Solenopsis Invicta Virus

<400> SEQUENCE: 65

Asn Met Phe Ser Tyr Trp Arg Ala Thr Met Cys Tyr Arg Ile Ala Ile
1               5                   10                  15

Val Lys Thr Ala Phe His Thr Gly Arg Leu Gly Ile Phe Phe Gly Pro
            20                  25                  30

Gly Tyr Lys Tyr Ile Leu Asp Leu Thr Asn Asp Thr Glu Ile Thr Ile
            35                  40                  45

Arg Val Pro Phe Val Ser Asn Lys
        50                  55

<210> SEQ ID NO 66
<211> LENGTH: 56
<212> TYPE: PRT
<213> ORGANISM: Solenopsis Invicta Virus

<400> SEQUENCE: 66

Ser Met Phe Lys Tyr Trp Thr Gly Ser Leu Val Tyr Thr Phe Lys Phe
1               5                   10                  15

Val Lys Thr Asp Tyr His Ser Gly Arg Val Glu Ile Ser Phe His Pro
            20                  25                  30

Phe Tyr Arg Ile Ile Val Asp Leu Arg Glu Lys Ser Glu Phe Ser Val
            35                  40                  45

Thr Ile Pro Phe Ile Ser Pro Val
        50                  55
```